(12) United States Patent
Stahmann et al.

(10) Patent No.: US 8,323,204 B2
(45) Date of Patent: Dec. 4, 2012

(54) MEDICAL EVENT LOGBOOK SYSTEM AND METHOD

(75) Inventors: Jeffrey E. Stahmann, Ramsey, MN (US); John D. Hatlestad, Maplewood, MN (US); Jesse W. Hartley, Lino Lakes, MN (US); Quan Ni, Shoreview, MN (US); Kent Lee, Singapore (SG)

(73) Assignee: Cardiac Pacemakers, Inc., St. Paul, MN (US)

( * ) Notice: Subject to any disclaimer, the term of this patent is extended or adjusted under 35 U.S.C. 154(b) by 175 days.

(21) Appl. No.: 12/403,880

(22) Filed: Mar. 13, 2009

(65) Prior Publication Data

US 2009/0177702 A1    Jul. 9, 2009

Related U.S. Application Data

(60) Continuation of application No. 10/920,568, filed on Aug. 17, 2004, now abandoned, which is a continuation-in-part of application No. 11/236,192, filed on Sep. 27, 2005, now Pat. No. 7,578,794, which is a division of application No. 10/331,175, filed on Dec. 27, 2002, now Pat. No. 6,949,075.

(60) Provisional application No. 60/504,749, filed on Sep. 18, 2003.

(51) Int. Cl.
*A61B 5/08* (2006.01)
*A61B 5/02* (2006.01)

(52) U.S. Cl. .................. 600/484; 600/529; 600/483

(58) Field of Classification Search .......... 600/529–543, 600/484, 513
See application file for complete search history.

(56) References Cited

U.S. PATENT DOCUMENTS

| 4,365,636 | A | 12/1982 | Barker |
| 4,519,395 | A | 5/1985 | Hrushesky |
| 4,562,841 | A | 1/1986 | Brockway et al. |
| 4,702,253 | A | 10/1987 | Nappholz et al. |
| 4,763,663 | A | 8/1988 | Uphold et al. |
| 4,813,427 | A | 3/1989 | Schlaefke et al. |
| 4,827,935 | A | 5/1989 | Geddes et al. |
| 4,830,008 | A | 5/1989 | Meer |
| 4,928,688 | A | 5/1990 | Mower |
| 4,930,517 | A | 6/1990 | Cohen et al. |

(Continued)

FOREIGN PATENT DOCUMENTS

EP    0940155    9/1999

(Continued)

OTHER PUBLICATIONS

Ajilore et al., *Nightcap: Laboratory and home-based evaluation of a portable sleep monitor*, 32 Psychophysiology, 32-98 (1995). Abstract only.

(Continued)

*Primary Examiner* — Navin Natnithithadha
(74) *Attorney, Agent, or Firm* — Hollingsworth Davis, LLC

(57) ABSTRACT

An event-based approach to collecting and organizing information associated with events affecting respiration is presented. The detection or prediction of an event affecting the respiration of a patient initiates acquisition of information associated with the event. The respiratory logbook system acquires information associated with the event during the event and during intervals proximate in time to the event. The information is organized as a respiratory log entry. The user can access the information by operating a user interface. The information may be presented in textual or graphical form.

18 Claims, 12 Drawing Sheets

U.S. PATENT DOCUMENTS

| | | | |
|---|---|---|---|
| 4,930,518 A | 6/1990 | Hrushesky | |
| 5,036,849 A | 8/1991 | Hauck et al. | |
| 5,105,354 A | 4/1992 | Nishimura | |
| 5,123,425 A | 6/1992 | Shannon, Jr. et al. | |
| 5,146,918 A | 9/1992 | Kallok et al. | |
| 5,165,417 A | 11/1992 | Murphy, Jr. | |
| 5,178,156 A | 1/1993 | Takishima et al. | |
| 5,187,657 A | 2/1993 | Forbes | |
| 5,203,348 A | 4/1993 | Dahl et al. | |
| 5,211,173 A | 5/1993 | Kallok et al. | |
| 5,215,082 A | 6/1993 | Kallok et al. | |
| 5,218,969 A | 6/1993 | Bredesen et al. | |
| 5,230,337 A | 7/1993 | Dahl et al. | |
| 5,233,983 A | 8/1993 | Markowitz | |
| 5,284,136 A | 2/1994 | Hauck et al. | |
| 5,301,677 A | 4/1994 | Hsung | |
| 5,313,953 A | 5/1994 | Yomtov et al. | |
| 5,334,222 A | 8/1994 | Salo et al. | |
| 5,335,657 A | 8/1994 | Terry, Jr. et al. | |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,447,164 A * | 9/1995 | Shaya et al. | 600/523 |
| 5,466,245 A | 11/1995 | Spinelli et al. | |
| 5,483,969 A | 1/1996 | Testerman et al. | |
| 5,485,851 A | 1/1996 | Erickson | |
| 5,487,755 A | 1/1996 | Snell et al. | |
| 5,522,862 A | 6/1996 | Testerman et al. | |
| 5,540,727 A | 7/1996 | Tockman et al. | |
| 5,545,186 A | 8/1996 | Olson et al. | |
| 5,545,202 A | 8/1996 | Dahl et al. | |
| 5,549,655 A | 8/1996 | Erickson | |
| 5,584,868 A | 12/1996 | Salo et al. | |
| 5,603,732 A | 2/1997 | Dahl et al. | |
| 5,645,570 A | 7/1997 | Corbucci | |
| 5,692,497 A | 12/1997 | Schnitzer et al. | |
| 5,738,102 A | 4/1998 | Lemelson | |
| 5,814,087 A | 9/1998 | Renirie | |
| 5,836,987 A | 11/1998 | Baumann et al. | |
| 5,844,680 A | 12/1998 | Sperling | |
| 5,855,593 A | 1/1999 | Olson et al. | |
| 5,861,011 A | 1/1999 | Stoop | |
| 5,888,187 A | 3/1999 | Jaeger et al. | |
| 5,891,023 A | 4/1999 | Lynn | |
| 5,911,218 A | 6/1999 | DiMarco | |
| 5,916,243 A | 6/1999 | KenKnight et al. | |
| 5,928,156 A | 7/1999 | Krumbiegel et al. | |
| 5,944,680 A | 8/1999 | Christopherson et al. | |
| 5,964,778 A | 10/1999 | Fugoso et al. | |
| 5,974,340 A | 10/1999 | Kadhiresan | |
| 6,026,320 A | 2/2000 | Carlson et al. | |
| 6,026,324 A | 2/2000 | Carlson et al. | |
| 6,044,298 A | 3/2000 | Salo et al. | |
| 6,045,513 A | 4/2000 | Stone et al. | |
| 6,047,211 A | 4/2000 | Swanson et al. | |
| 6,055,454 A | 4/2000 | Heemels | |
| 6,064,910 A | 5/2000 | Andersson et al. | |
| 6,076,015 A | 6/2000 | Hartley et al. | |
| 6,091,973 A | 7/2000 | Colla et al. | |
| 6,099,479 A | 8/2000 | Christopherson et al. | |
| 6,116,241 A | 9/2000 | Huygen et al. | |
| 6,120,441 A | 9/2000 | Griebel | |
| 6,126,611 A | 10/2000 | Bourgeois et al. | |
| 6,128,534 A | 10/2000 | Park et al. | |
| 6,132,384 A | 10/2000 | Christopherson et al. | |
| 6,139,505 A | 10/2000 | Murphy, Jr. | |
| 6,141,581 A | 10/2000 | Olson et al. | |
| 6,141,590 A | 10/2000 | Renirie et al. | |
| 6,142,950 A * | 11/2000 | Allen et al. | 600/529 |
| 6,168,568 B1 | 1/2001 | Gavriely | |
| 6,190,326 B1 | 2/2001 | McKinnon et al. | |
| 6,216,702 B1 | 4/2001 | Gjersoe | |
| 6,221,011 B1 | 4/2001 | Bardy | |
| 6,240,316 B1 | 5/2001 | Richmond et al. | |
| 6,251,126 B1 | 6/2001 | Ottenhoff et al. | |
| 6,258,039 B1 | 7/2001 | Okamoto et al. | |
| 6,259,947 B1 | 7/2001 | Olson et al. | |
| 6,263,244 B1 | 7/2001 | Mann et al. | |
| 6,264,606 B1 | 7/2001 | Ekwall | |
| 6,269,269 B1 | 7/2001 | Ottenhoff et al. | |
| 6,270,457 B1 | 8/2001 | Bardy | |
| 6,272,377 B1 | 8/2001 | Sweeney et al. | |
| 6,275,727 B1 | 8/2001 | Hopper et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,351,669 B1 | 2/2002 | Hartley et al. | |
| 6,351,670 B1 | 2/2002 | Kroll | |
| 6,353,759 B1 | 3/2002 | Hartley et al. | |
| 6,358,203 B2 | 3/2002 | Bardy | |
| 6,363,270 B1 | 3/2002 | Colla et al. | |
| 6,368,284 B1 | 4/2002 | Bardy | |
| 6,368,287 B1 | 4/2002 | Hadas | |
| 6,371,922 B1 | 4/2002 | Baumann et al. | |
| 6,375,621 B1 | 4/2002 | Sullivan | |
| 6,390,091 B1 | 5/2002 | Banner et al. | |
| 6,397,845 B1 | 6/2002 | Burton | |
| 6,398,728 B1 | 6/2002 | Bardy | |
| 6,409,675 B1 | 6/2002 | Turcott | |
| 6,411,848 B2 | 6/2002 | Kramer et al. | |
| 6,415,175 B1 | 7/2002 | Conley et al. | |
| 6,415,183 B1 | 7/2002 | Scheiner et al. | |
| 6,424,865 B1 | 7/2002 | Ding | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,449,503 B1 | 9/2002 | Hsu | |
| 6,449,504 B1 | 9/2002 | Conley et al. | |
| 6,456,256 B1 | 9/2002 | Amundson et al. | |
| 6,459,929 B1 | 10/2002 | Hopper et al. | |
| 6,480,733 B1 | 11/2002 | Turcott | |
| 6,487,443 B2 | 11/2002 | Olson et al. | |
| 6,542,775 B2 | 4/2003 | Ding et al. | |
| 6,574,507 B1 | 6/2003 | Bonnet | |
| 6,580,944 B1 | 6/2003 | Katz et al. | |
| 6,589,187 B1 * | 7/2003 | Dirnberger et al. | 600/508 |
| 6,589,188 B1 | 7/2003 | Street et al. | |
| 6,597,951 B2 | 7/2003 | Kadhiresan et al. | |
| 6,641,542 B2 | 11/2003 | Cho et al. | |
| 6,741,885 B2 | 5/2004 | Park et al. | |
| 6,773,404 B2 | 8/2004 | Poezevera et al. | |
| 6,810,287 B2 | 10/2004 | Zhu et al. | |
| 6,820,618 B2 | 11/2004 | Banner et al. | |
| 6,881,192 B1 * | 4/2005 | Park | 600/529 |
| 6,895,275 B2 * | 5/2005 | Markowitz et al. | 607/18 |
| 6,915,157 B2 * | 7/2005 | Bennett et al. | 600/513 |
| 6,949,075 B2 | 9/2005 | Hatlesad et al. | |
| 6,964,641 B2 | 11/2005 | Cho et al. | |
| 7,025,730 B2 * | 4/2006 | Cho et al. | 600/529 |
| 7,089,936 B2 | 8/2006 | Madaus et al. | |
| 7,092,757 B2 | 8/2006 | Larson et al. | |
| 7,115,097 B2 | 10/2006 | Johnson | |
| 7,155,275 B2 | 12/2006 | Linder et al. | |
| 7,207,945 B2 | 4/2007 | Bardy | |
| 7,225,013 B2 | 5/2007 | Geva et al. | |
| 7,252,640 B2 * | 8/2007 | Ni et al. | 600/538 |
| 7,314,451 B2 | 1/2008 | Halperin et al. | |
| 7,359,837 B2 | 4/2008 | Drew | |
| 7,572,225 B2 | 8/2009 | Stahmann et al. | 600/484 |
| 7,766,842 B2 * | 8/2010 | Ni et al. | 600/538 |
| 7,983,745 B2 * | 7/2011 | Hatlestad et al. | 600/513 |
| 2002/0151812 A1 | 10/2002 | Scheiner et al. | |
| 2002/0161412 A1 | 10/2002 | Sun et al. | |
| 2002/0188213 A1 * | 12/2002 | Bardy | 600/509 |
| 2002/0193697 A1 * | 12/2002 | Cho et al. | 600/529 |
| 2002/0193839 A1 | 12/2002 | Cho et al. | |
| 2003/0023184 A1 | 1/2003 | Pitts-Crick et al. | |
| 2003/0055461 A1 | 3/2003 | Girouard et al. | |
| 2003/0100925 A1 | 5/2003 | Pape et al. | |
| 2003/0105497 A1 * | 6/2003 | Zhu et al. | 607/17 |
| 2003/0139780 A1 | 7/2003 | Markowitz et al. | |

| | | | |
|---|---|---|---|
| 2003/0153953 | A1 | 8/2003 | Park et al. |
| 2003/0153954 | A1 | 8/2003 | Park et al. |
| 2003/0153955 | A1 | 8/2003 | Park et al. |
| 2003/0153956 | A1 | 8/2003 | Park et al. |
| 2003/0163059 | A1 | 8/2003 | Poezevera et al. |
| 2003/0195571 | A1 | 10/2003 | Burnes et al. |
| 2003/0199945 | A1 | 10/2003 | Ciulla |
| 2003/0204213 | A1 | 10/2003 | Jensen et al. |
| 2004/0002742 | A1 | 1/2004 | Florio |
| 2004/0030362 | A1 | 2/2004 | Hill et al. |
| 2004/0059240 | A1* | 3/2004 | Cho et al. ............... 600/532 |
| 2004/0088027 | A1 | 5/2004 | Burnes et al. |
| 2004/0102814 | A1 | 5/2004 | Sorensen et al. |
| 2004/0111040 | A1 | 6/2004 | Ni et al. |
| 2004/0116981 | A1 | 6/2004 | Mazar |
| 2004/0122487 | A1 | 6/2004 | Hatlestad et al. |
| 2004/0122488 | A1 | 6/2004 | Mazar et al. |
| 2004/0127807 | A1 | 7/2004 | Hatlesad et al. |
| 2004/0128161 | A1 | 7/2004 | Mazar et al. |
| 2004/0133079 | A1 | 7/2004 | Mazar et al. |
| 2004/0138719 | A1 | 7/2004 | Cho et al. |
| 2005/0043772 | A1 | 2/2005 | Stahmann et al. |
| 2005/0080348 | A1* | 4/2005 | Stahmann et al. ............ 600/529 |
| 2007/0088399 | A1 | 4/2007 | Linder et al. |
| 2009/0124917 | A1* | 5/2009 | Hatlestad et al. ............ 600/529 |

FOREIGN PATENT DOCUMENTS

| | | |
|---|---|---|
| EP | 1151718 | 11/2001 |
| EP | 1172125 | 1/2002 |
| WO | WO 99/04841 | 4/1999 |
| WO | WO 00/01438 | 1/2000 |
| WO | WO 00/17615 | 3/2000 |
| WO | WO 02/087696 | 11/2002 |

OTHER PUBLICATIONS

Balaban et al., *Feasibility of Screening for Sleep Apnea Using Pacemaker Impedance Sensor*, NASPE (2001).
Bradley et al., *Pathophysiologic and Therapeutic Implications of Sleep Apnea in Congestive Heart Failure*, 3 J. Cardiac Failure 223-240 (1996).
Bradley et al., *Sleep Apnea and Heart Failure, Park I: Obstructive Sleep Apnea*, 107 Circulation 1671-1678 (2003).
Garrigue et al., *Night Atrial Overdrive with DDD Pacing: a New Therapy for Sleep Apnea Syndrome*, NASPE (2000).
Garrigue et al., *Night Atrial Overdrive with DDD Pacing Results in a Significant Reduction of Sleep Apnea Episodes and QOL Improvement in Heart Failure Patients*, NASPE (2001).
Garrigue et al., *Benefit of Atrial Pacing in Sleep Apnea Syndrome*, 346 N. Engl. J. Med. 404-412 (2002).
Guidant System Guide, Vitality AVT™, Automatic Implantable Cardioverter Defibrillator Model A135, Part 1 of 2, Chapter 7, pp. 7-1 through 7-30, 2003.
Hilton et al., *Evaluation of Frequency and Time-frequency Spectral Analysis of Heart Rate Variability as a Diagnostic Marker of the Sleep Apnea Syndrome*, 37 Med. Biol. Eng. Comput. 760-769 (1999). Abstract only.
Javaheri et al., *Sleep Apnea in 81 Ambulatory Male Patients with Stable Heart Failure: Types and Their Prevalences, Consequences, and Presentations*, 97 Circulation 2154-2159 (1998).
Javaheri et al., *A Mechanism of Central Sleep Apnea in Patients With Heart Failure*,341 N. Engl. J. Med. 949-954 (1999).
Roche et al., *Screening of Obstructive Sleep Apnea Syndrome by Heart Rate Variability Analysis*, 100 Circulation 1411-1455 (1999).
Vanninen et al., *Cardiac Sympathovagal Balance During Sleep Apnea Episodes*, 16 Clin. Physiol. 209-216 (1996).
Verrier et al., *Sleep, dreams, and sudden death: the case for sleep as an autonomic stress test for the heart*, 31 Cardiovascular Research 181-211 (1996).
Verrier et al., *Sleep Related Cardiovascular Risk: New Home-Based Monitoring Technology for Improved Diagnosis and Therapy*, 2 A.N.E. 158-175 (1997).
Waldemark et al., *Detection of Apnea using Short Window FFT Technique and Artificial Neural Network*, 3390 SPIE International Society for Optical Engineering 122-133 (1998).
Young et al., *The Occurrence of Sleep-Disordered Breathing Among Middle Aged Adults*, N. Engl. J. Med. 1230-1235 (1993).
Office Action from U.S. Appl. No. 10/920,568 dated Dec. 27, 2007, 20 pages.
Office Action from U.S. Appl. No. 10/920,568 dated Nov. 14, 2008, 10 pages.
Office Action from U.S. Appl. No. 11/236,192 dated Aug. 16, 2007, 7 pages.
Office Action from U.S. Appl. No. 11/236,192 dated Mar. 25, 2008, 7 pages.
Office Action from U.S. Appl. No. 11/236,192 dated Oct. 29, 2008, 8 pages.
Office Action from U.S. Appl. No. 10/331,175 dated Jul. 1, 2004, 14 pages.
Office Action from U.S. Appl. No. 10/331,175 dated Jan. 11, 2005, 8 pages.
Jan. 21, 2011, File History for U.S. Appl. No. 12/545,652.
Notice of Allowance dated May 6, 2005 from U.S. Appl. No. 10/331,175, 4 pages.
Office Action Response dated Apr. 6, 2005 from U.S. Appl. No. 10/331,175, 10 pages.
Office Action Response dated Oct. 1, 2004 from U.S. Appl. No. 10/331,175, 10 pages.
Notice of Allowance dated Apr. 30, 2009 from U.S. Appl. No. 11/236,192, 7 pages.
Office Action Response dated Feb. 25, 2009 from U.S. Appl. No. 11/236,192, 12 pages.
Interview Summary dated Feb. 17, 2009 from U.S. Appl. No. 11/236,192, 2 pages.
Office Action dated Oct. 29, 2008 from U.S. Appl. No. 11/236,192, 7 pages.
Office Action Response dated Aug. 25, 2008 from U.S. Appl. No. 11/236,192, 12 pages.
Office Action dated Jun. 13, 2008 from U.S. Appl. No. 11/236,192, 3 pages.
Office Action Response dated May 27, 2008 from U.S. Appl. No. 11/236,192, 11 pages.
Office Action Response dated Dec. 17, 2007 from U.S. Appl. No. 11/236,192, 8 pages.
International Preliminary Examination Report dated Jul. 31, 2006 from PCT Application No. PCT/US03/040968, 5 pages.
Office Action dated Jan. 29, 2010 from European Application No. 03808539.5, 4 pages.
Office Action Response dated Aug. 9, 2010 from European Application No. 03808539.5, 9 pages.
Office Action dated Dec. 14, 2009 from Japanese Application No. 2004-565641, 3 pages.
Office Action dated Nov. 14, 2008 from U.S. Appl. No. 10/920,568, 8 pages.
Office Action Response dated May 30, 2008 from U.S. Appl. No. 10/920,568, 11 pages.
Office Action dated Dec. 27, 2007 from U.S. Appl. No. 10/920,568, 10 pages.
Office Action Response dated Nov. 23, 2007 from U.S. Appl. No. 10/920,568, 5 pages.
Office Action dated Sep. 17, 2007 from U.S. Appl. No. 10/920,568, 6 pages.
Steven Lehrer, M.D., Understanding Lung Sounds, Second Ed., Copyright 1993, 1984 by W.B. Saunders Company, pp. 91-105.
J.P. Saul, R.J. Cohen, Respiratory Sinus Arrhythmia, Vagal Control of the Heart: Experimental Basis and Clinical Implications edited by M.N. Levy, P.J. Schwartz, copyright 1994, Futura Publishing Co., In., Armonk, NY, pp. 511-537.
M.R. Cowie, D.A. Wood, A.J.S. Coats, S.G. Thompson, V. Suresh, P.A. Poole-Wilson, G.C. Sutton, Survival of Patients with a New Diagnosis of Heart Failure: A Population Based Study, Heart 2000; 83:505-510.
Office Action dated Oct. 13, 2010 from U.S. Appl. No. 12/545,652, 6 pages.
Office Action Response dated Nov. 9, 2010 from U.S. Appl. No. 12/545,652, 5 pages.
File History for European Application No. 03808539.5 as retrieved the European Patent Office Electronic File System on Apr. 25, 2011, 122 pages.
Office Action dated Sep. 24, 2012 for European Application No. 03808539.5, 5 pages.

* cited by examiner

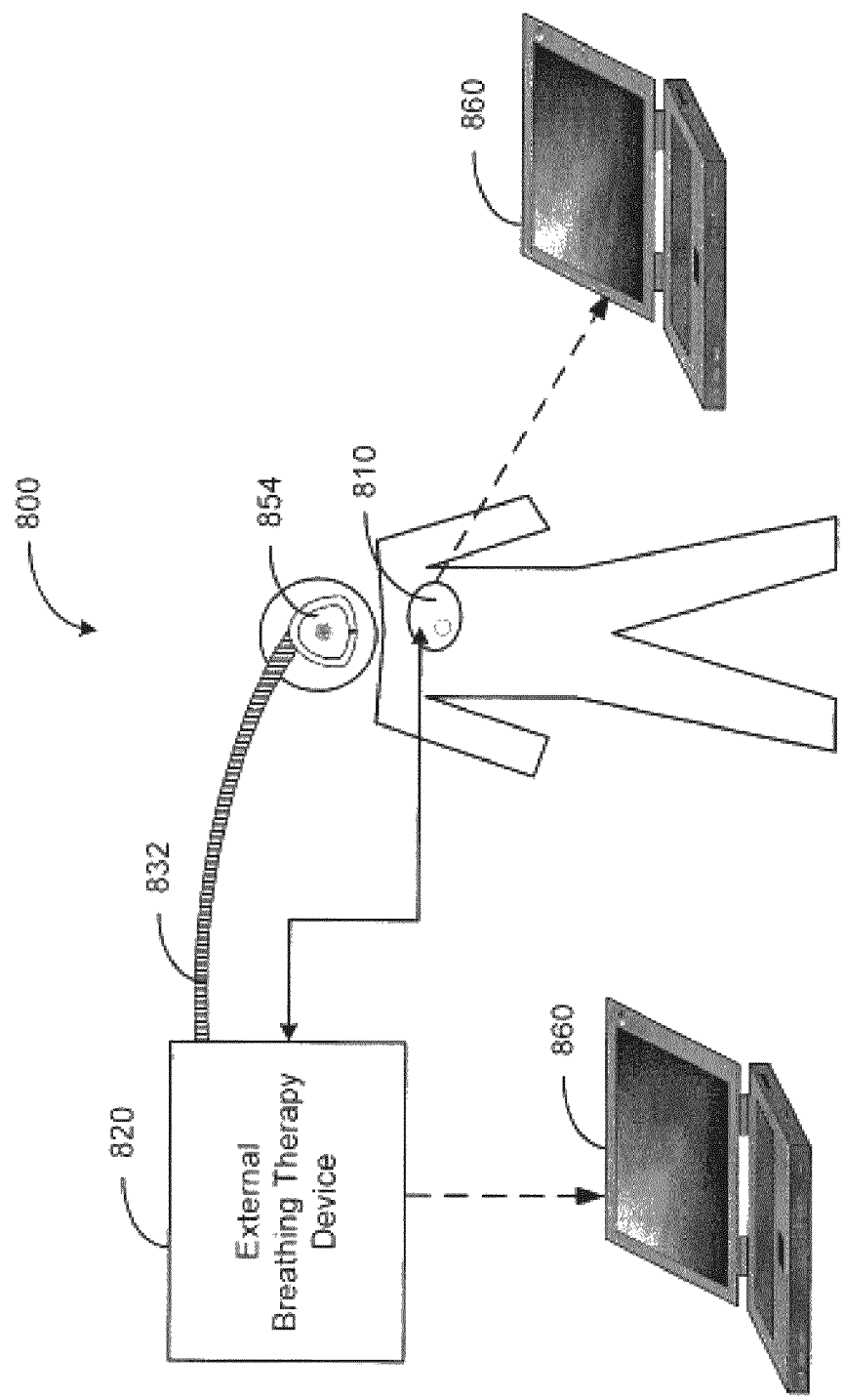

MEDICAL EVENT LOGBOOK SYSTEM AND METHOD

RELATED PATENT DOCUMENTS

This application is a continuation under 35 U.S.C. §120 of U.S. application Ser. No. 10/920,568 filed Aug. 17, 2004, now abandoned which claims the benefit under 35 U.S.C. §119(e) of Provisional U.S. Application Ser. No. 60/504,749, filed on Sep. 18, 2003, both of the foregoing applications being incorporated herein by reference in their entireties. This application is also a continuation-in-part under 35 U.S.C. §120 of application Ser. No. 11/236,192, filed Sep. 27, 2005, U.S. Pat. No. 7,578,794, which is a divisional under 35 U.S.C. §120 of application Ser. No. 10/331,175, filed Dec. 27, 2002, U.S. Pat. No. 6,949,075. This application claims priority to all of the foregoing applications as indicated.

FIELD OF THE INVENTION

The present invention relates to acquiring and organizing information related to medical events affecting the patient.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiratory system, through the breathing mechanism, performs the function of exchanging these gases with the external environment. Together, the cardiac and respiratory systems form a larger anatomical and functional unit denoted the cardiopulmonary system.

Various disorders may affect the cardiovascular, respiratory, and other physiological systems. For example, heart failure is a clinical syndrome that impacts a number of physiological processes. Heart failure is an abnormality of cardiac function that causes cardiac output to fall below a level adequate to meet the metabolic demand of peripheral tissues and internal organs. Heart failure is often referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other conditions.

Chronic obstructive pulmonary disease generally develops over many years, typically from exposure to cigarette smoke, pollution, or other irritants. Over time, the elasticity of the lung tissue is lost, and the lungs become distended, unable to expand and contract normally. As the disease progresses, breathing becomes labored, and the patient grows progressively weaker. Other types of non-rhythm related pulmonary diseases or disorders include restrictive pulmonary diseases, infections pulmonary diseases, diseases of the pleural cavity, and pulmonary vasculature, for example.

Breathing disorders include various forms of rhythm-related disorders such as sleep apnea and hypopnea, among other forms. Disordered breathing is a respiratory system condition that affects a significant percentage of patients between 30 and 60 years. Disordered breathing, including apnea and hypopnea, may be caused, for example, by an obstructed airway, or by derangement of the signals from the brain controlling respiration. Disordered breathing occurs when a patient experiences insufficient respiration with or without respiratory effort. Disordered breathing can originate from a deficiency in the central nervous system (central disordered breathing) or from an obstructed airway (obstructive disordered breathing). Lack of respiratory effort may result from a disruption of signals from the central nervous system to the respiratory muscles.

Central disordered breathing events are characterized by insufficient respiration and a concurrent lack of respiratory effort. Because the central nervous system signals that control breathing are interrupted, the patient's natural breathing reflex is not triggered. The patient makes no effort to breath or the respiratory effort is otherwise disrupted. Respiration ceases or is insufficient during the disordered breathing event.

An obstructive disordered breathing event may occur due to an obstruction of a patient's airway. For example, the patient's the tongue or other soft tissue of the throat may collapse into the patient's airway. The breathing reflex is triggered, but respiration is disrupted because of the occluded airway. Disordered breathing events may include central disordered breathing events, obstructive disordered breathing events, or mixed disordered breathing events that are a combination of obstructive and central types.

Sleep disordered breathing is particularly prevalent and is associated with excessive daytime sleepiness, systemic hypertension, increased risk of stroke, angina and myocardial infarction. Disordered breathing can be particularly serious for patients concurrently suffering from cardiovascular deficiencies.

Various types of disordered respiration have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

Because of the complex interactions between the cardiovascular, pulmonary, and other physiological systems as well as the need for early detection of various disorders, an effective approach to acquiring and organizing information related to respiratory events is desired. The present invention fulfills these and other needs, and addresses other deficiencies of prior art implementations and techniques

SUMMARY OF THE INVENTION

Embodiments of the invention relate to acquiring and organizing information related to medical events affecting the patient. One embodiment of the invention involves a method for organizing medical information. The method involves detecting or predicting a respiratory event of a patient. Responsive to the detection or prediction of the respiratory event, collection of medical information associated with the respiratory event is initiated. The medical information is collected and organized as a respiratory event log entry. At least one of detecting or predicting the respiratory event, collecting the medical information and organizing the medical information is performed implantably.

In accordance with another embodiment of the invention, a method for accessing medical information involves collecting medical information associated with respiratory events. The collection of medical information associated with respiratory events includes initiating, responsive to the detection or prediction of the respiratory event, collection of medical information associated with each respiratory event. The medical information is collected and organized a respiratory logbook. A user interface is provided for accessing the respiratory logbook. At least one of detecting or predicting the respiratory event, collecting the medical information and organizing the medical information is performed implantably.

Another embodiment of the invention involves a method for organizing respiratory information associated with medical events. Responsive to the detection and/or prediction of a medical event, the system initiates collection of respiratory information associated with the medical event. The respiratory information is collected and organized as a medical event log entry. At least one of detecting or predicting the medical event, collecting the respiratory information and organizing the respiratory information is performed implantably.

In accordance with a further embodiment of the invention, a method for accessing respiratory information associated with medical events of a patent involves collecting and organizing respiratory information associated with medical events. Collection of the respiratory information is implemented by initiating, responsive to the detection or prediction of a medical event, collection of respiratory information associated with each medical event. The respiratory information is collected and organized in a medical event logbook. A user interface provides access to the medical event logbook. At least one of detecting or predicting the medical event, collecting the respiratory information and organizing the respiratory information is performed implantably.

Yet another embodiment involves a method for organizing medical event information. According to this method, a medical event is predicted. The system collects information associated with conditions affecting the patient prior to the occurrence of the medical event. The medical event is detected, and the system collects information during the medical event. The collected information is organized as a medical event log entry. At least one of detecting the medical event, predicting the medical event, collecting the respiratory information and organizing the respiratory information is performed implantably.

In accordance with another embodiment of the invention, a medical event logbook system includes an event detector configured to detect or predict a medical event. A data acquisition unit is coupled to the event detector and is configured to collect, responsive to the detection or prediction of the medical event, respiratory information associated with the medical event. The system also includes processor configured to organize the acquired respiratory information as a medical event log entry. At least one of the event detector, the data acquisition unit, and the processor includes an implantable component.

In accordance with a further embodiment, a respiratory event logbook system includes an event detector configured to detect or predict a respiratory event affecting the patient. A data acquisition unit is coupled to the event detector and is configured to collect medical information associated with the respiratory event responsive to the detection or prediction of the respiratory event. The system includes a processor configured to organize the collected medical information associated with the respiratory event as a respiratory event log entry. At least one of the event detector, the data acquisition unit, and the processor includes an implantable component.

BRIEF DESCRIPTION OF THE DRAWINGS

FIG. 8 is a block diagram illustrating a medical system including a patient-internal device cooperating with a patient-external device to acquire and organize information in a respiratory logbook in accordance with embodiments of the invention;

Figures 1A, 1B:
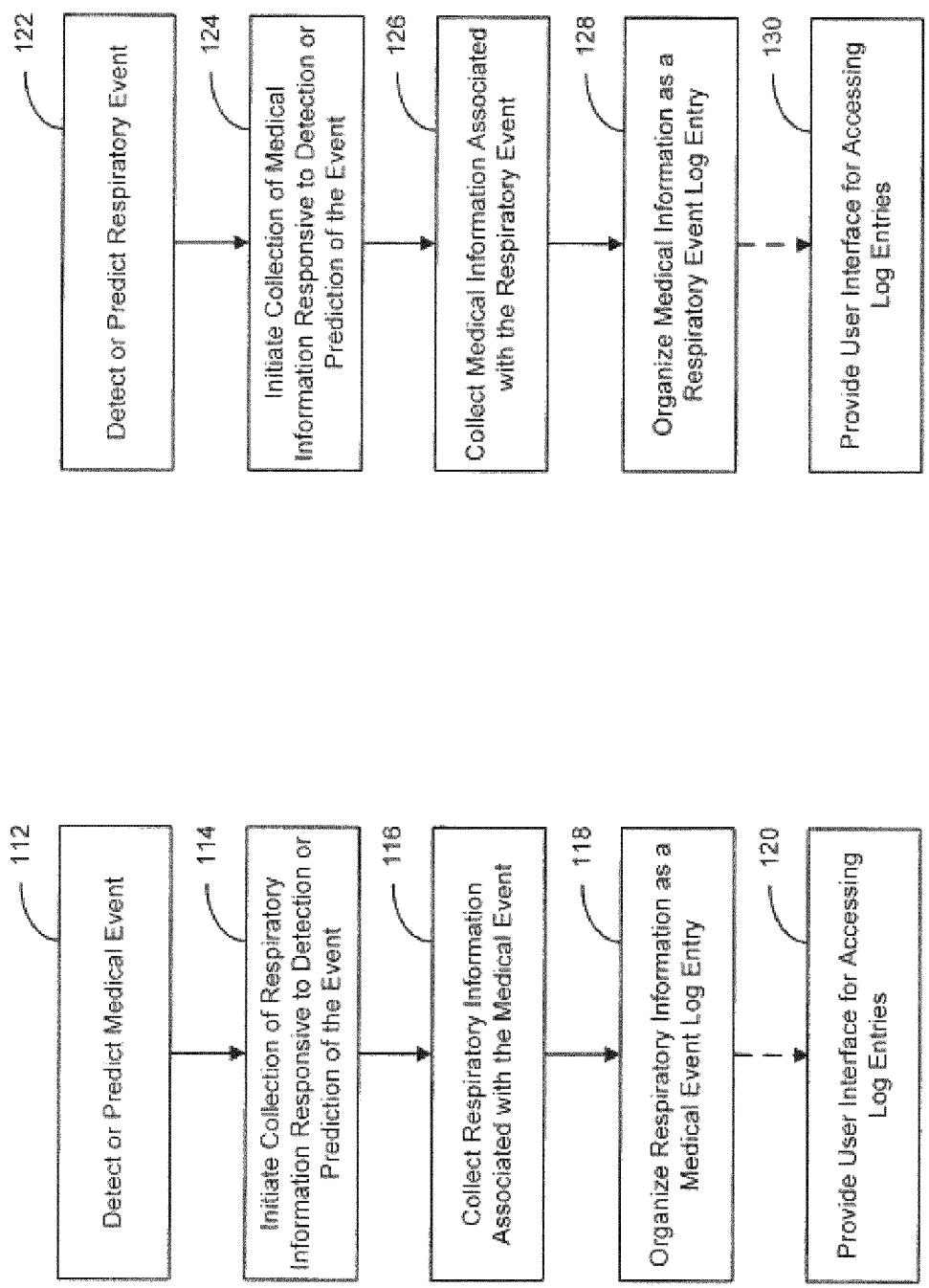
FIGS. 1A-1C are flowcharts of methods for acquiring and organizing information as event log entries in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown by way of illustration, various embodiments in which the invention may be practiced. It is to be understood that other embodiments may be utilized and structural and functional changes may be made without departing from the scope of the present invention.

Early detection and diagnosis of various types of diseases and syndromes may enhance the likelihood of successful treatment. However, the onset of some types of medical disorders may be very gradual and/or occur in discrete episodes, or at times that are inconvenient for collecting data, making early detection more difficult. Early diagnosis may depend on the recognition of changes in various physiological conditions that may not be apparent during yearly or even monthly check-ups.

In one example, breathing rhythm disorders often are present only while the patient is asleep. Sleep disordered breathing assessments depend upon acquiring data while the patient is asleep. Diagnosis of sleep disorders typically involves the use of a polysomnographic sleep study performed at a dedicated sleep facility. However, such studies are costly, inconvenient to the patient, and may not accurately represent the patient's typical sleep behavior.

In a polysomnographic sleep study, the patient is instrumented for data acquisition and observed by trained personnel. Assessment of sleep disordered breathing in a laboratory setting presents a number of obstacles to acquiring an accurate picture of events occurring during sleep. For example, spending a night in a sleep laboratory typically causes a patient to experience a condition known as "first night syndrome," involving disrupted sleep during the first few nights in an unfamiliar location. In addition, sleeping while instrumented and observed may not result in a realistic perspective of the patient's normal sleep patterns.

Many types of medical events occur in discrete episodes. Periodic monitoring of patient information may not be the most effective way to collect data related to discrete events. Due to the transient nature of events, collecting a snapshot of patient information on a daily or weekly basis, or according to another time schedule, may not always capture event information. Continuous monitoring allows detection of aperiodic or infrequent events. However, the amount of memory required for storing patient information on a substantially continuous basis may be prohibitive.

Embodiments of the invention are directed to an event-based approach to storing and organizing information associated with medical and/or respiratory events. A logbook entry includes information, e.g., respiratory and/or medical information, acquired during time intervals surrounding an event. In one aspect of the invention, respiratory information collected in response to a medical event is organized as a medical event log entry. In another aspect of the invention, medical information collected in response to a respiratory event is organized as a respiratory event log entry.

A number of logbook entries form a logbook that may be accessed by the user through a user interface. The processes described herein enhance the ability to acquire and store information about discrete events. Further, the event logbook format provides an intuitive approach for organizing and presenting the information to patients or physicians.

FIG. 1A is a flowchart illustrating a method of acquiring and organizing respiratory information collected in response to a medical event. The medical event may involve various types of events affecting one or more of the respiratory system, cardiovascular system, nervous system, muscle systems, and/or other physiological systems or combinations of physiological systems of the patient. The system implementing the method may be programmable to detect or predict a particular type of event, for example, a cardiac event, such as cardiac arrhythmia or an ectopic beat. The system may collect information about one or more respiratory parameters during, before and/or after the medical event.

In response to the detection or prediction 112 of the medical event, collection 114 of respiratory information for the medical event logbook entry is initiated. In some embodiments, the respiratory information is collected 116 during the event. In other embodiments, the respiratory information is collected 116 during the event and during a time period proximate to the event. Information may be collected during the event, during a period of time preceding the event, and/or during a period of time following the event. In some embodiments, the information may be collected prior to the prediction or detection of the event.

To facilitate collection of respiratory information preceding the prediction or detection of the event, respiratory conditions may be monitored, e.g., on a continuous or periodic basis, and stored in a temporary buffer. Temporary storage is required to provide information prior to the event prediction or detection, e.g., onset data. The size of the temporary storage buffer may vary according to the medical events for which onset data is desired. Due to the varied nature of onset data requirements and the reality of limited storage in the system, the system may allow different onset data lengths and different sampling rates for the temporarily stored data. In the preferred embodiment the system would use a circular buffer to store the temporary data such that the oldest data is replaced by the newest data.

Once initiated, collection of respiratory information, which may involve storage of the information in long term memory, may be performed on a substantially continuous basis, or it may be performed periodically. Long term storage of data acquired periodically may be beneficial when the event is relatively prolonged, such an in the case of a disease or disorder that may linger for several days or weeks. The type of data collected, data collection frequency, and/or data collection intervals may be selectable by the user. Further, the system may be programmable to use different data collection regimens under different conditions over the course of the event. For example, the system may be programmable to collect data more frequently during sleep or during particular stages of the disease progression, for example. The system may be programmed to collect data on a continuous basis during some time intervals, and periodically during other time intervals, for example.

Collecting information preceding the event facilitates enhanced identification of conditions that may be used to detect or predict the occurrence of future events. For example, acquiring information preceding a medical event allows for the identification and assessment of physiological conditions present immediately before and leading up to the medical event. The identification of precursor conditions for medical events may facilitate increased sensitivity and/or accuracy in detecting or predicting occurrences of the future events.

The acquired respiratory information is organized 118 as a medical event log entry. A medical event logbook may comprise a number of entries, each entry corresponding to a separate medical event. The medical events represented in the medical event logbook may comprise, for example, cardiovascular system events, nervous system events, respiratory system events, or any other medical events affecting the patient. The event entries included in medical event log may be organized according to various categories, including for example, event type, event time/date, order of occurrence of the event, therapy provided to treat the event, among other categories. The selection of categories used to organize the information may be programmable by the user. The organized information may be stored in long term memory, displayed, printed, and/or transmitted to a separate device. In one approach, the medical event comprises a cardiac event. Respiratory information collected before, during and/or after the cardiac event may be stored as a log entry in a cardiac arrhythmia logbook, for example.

In one embodiment of the invention, the collected information for the events is optionally accessible 120 through an interactive user interface. Selection of events to the accessed may involve a hierarchical selection menu, or other selection method, for example. In one implementation, the user may select a log entry from the menu by activating an input mechanism. Upon selection of the log entry, the user interface may provide graphical or textual depictions of the collected respiratory information associated with the medical event.

FIG. 1B is a flow chart for an embodiment involving collecting medical information associated with a respiratory event. The respiratory event may be detected or predicted 122. The event may include any detectable or predictable respiratory event, such as disordered breathing (apnea, hypopnea, tachypnea), coughing and/or breathing irregularities associated with pulmonary diseases and disorders such as asthma, pulmonary edema, chronic obstructive pulmonary disease, and/or pleural effusion, among others.

In response to the detection or prediction 122 of the respiratory event, collection 124 of medical information for the respiratory event logbook entry is initiated. The medical information may be collected 124 during the event and/or during a time period proximate to the event. Information may be collected during the event, during a period of time preceding the event, and/or during a period of time following the event. In some embodiments, the information may be collected prior to the prediction or detection of the respiratory event.

To facilitate collection of medical information preceding the prediction or detection of the respiratory event, the medical information may be monitored, e.g., on a continuous or periodic basis, and stored in a temporary buffer. Temporary storage is required to provide information prior to the event prediction or detection, e.g., onset data. The duration of the temporary storage may vary according to the respiratory events for which onset data is desired. For example, temporary storage of about one minute may be sufficient to understand onset conditions for an obstructive an apnea event whereas temporary storage of about one day may be required to understand onset conditions for an asthma event.

Due to the varied nature of onset data requirements and the reality of limited storage in the system, the system may allow different onset data lengths and different sampling rates for the temporarily stored data. In a preferred embodiment, the system uses a circular buffer to store the temporary data such that the oldest data is replaced by the newest data.

Once initiated, collection of respiratory information, which may involve storage of the information in long term memory, may be performed on a substantially continuous basis, or it may be performed during discrete intervals. Long term collection of data on a periodic basis may be beneficial when the event is relatively prolonged, such an in the case of a disease or disorder that may linger for several days or weeks. Various collection parameters, such as the type of data collected, data collection frequency, and/or data collection intervals may be selectable by the user. Further, the system may be programmable to use different data collection regimens under different conditions over the course of the event. For example, the system may be programmed to collect data more frequently during sleep or during particular stages of the disease progression, for example. The system may be programmed to collect data on a substantially continuous basis during some time intervals, and periodically during other time intervals, for example.

Collecting medical information preceding the respiratory event facilitates enhanced identification of conditions that may be used to detect or predict the occurrence of future events. For example, acquiring information preceding the event affecting patient respiration allows for the identification and assessment of physiological conditions present immediately before and leading up to the event. In one scenario, the patient may experience a period of hyperventilation prior to an apnea event. Collecting respiratory information prior to the apnea event allows the identification of hyperventilation as a precursor condition. The identification of precursor conditions for apnea facilitate increased sensitivity and/or accuracy in detecting or predicting future occurrences of apnea.

Additionally, or alternatively, medical information preceding the respiratory event may provide insight into conditions that predispose the patient to certain respiratory events. Acquiring information preceding the event may provide allow identification of the triggering or causal factors of the event. For example, an asthma attack may be induced by increased exercise or a sudden change in ambient temperature, e.g., the patient moving from a warmer location to a colder location. Collection of medical information preceding the asthma attack allows the factors that precipitate the respiratory event to be identified. Such information may be used to enhance the detection and/or prediction of future events.

Information collected following the event may be used to assess the acute effects of the event. Episodes of disordered breathing, for example, may be associated with acute physiological effects, including negative intrathoracic pressure, hypoxia, and arousal from sleep. Such effects may be detectable for a period of time following the respiratory event.

For example, obstructive sleep apneas are typically terminated by arousal from sleep that occurs several seconds after the apneic peak, allowing the resumption of airflow. Coincident with arousal from sleep, and continuing for some period of time after termination of the event, surges in sympathetic nerve activity, blood pressure, and heart rate occur.

During obstructive apnea events, the effort to generate airflow increases. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses. Collection of data following obstructive sleep apnea events may be used to determine the presence and/or severity of the secondary responses to obstructive apnea events. The post-event information enhances the ability to evaluate the impact of the secondary responses upon the patient.

As previously described, obstructive sleep apnea events are typically terminated by arousal from sleep. However, arousals are not usually required for the resumption of breathing in central sleep apnea events. In the case of central apnea events, the arousals follow the initiation of breathing. Arousals following central apnea events may facilitate the development of oscillations in ventilation by recurrently stimulating hyperventilation and reducing $PaCO_2$ below the apneic threshold. Once triggered, the pattern of alternating hyperventilation and apnea may be sustained by the combination of increased respiratory drive, pulmonary congestion, arousals, and apnea-induced hypoxia causing $PaCO_2$ oscillations above and below the apneic threshold. Shifts in the patient's state of consciousness, particularly with repeated arousals, may further destabilize breathing. Collecting information during central apnea events and before and/or after the occurrence of the events may allow identification of the oscillations associated with central apnea.

The collected medical information, which may be stored in long term memory, transmitted, printed and/or displayed is organized as a respiratory logbook entry 128. The medical information may include various physiological and non-physiological data. For example, respiratory system data, cardiovascular system data, nervous system data, posture, activity, medical history data, environmental data (temperature, altitude, air quality) and other types of medical information may be organized as a respiratory logbook entry. The respiratory logbook entry may be stored, transmitted, printed and/or displayed.

A respiratory event logbook may comprise a number of entries, each entry corresponding to a separate respiratory event. The event entries included in medical event log may be organized according to various categories, including for example, event type, event time/date, order of occurrence of the event, therapy provided to treat the event, among other categories. The selection of categories used to organize the information may be programmable by the user. The organized information may be stored in long term memory, displayed, printed, and/or transmitted to a separate device.

The collected information for the events may be optionally accessible 130 through an interactive user interface. The interactive user interface may provide access to one or more log entries through activation of a selection process, involving a hierarchical selection menu, or other selection method, for example. In one implementation, the user may select a log entry from the menu by activating an input mechanism. Upon selection of the log entry, the user interface may provide graphical or textual depictions of the collected respiratory information associated with the medical event.

Relating to both FIGS. 1A and 1B, the event information of the logbook may be stored in long term memory using various storage methodologies. For example, the logbook may utilize a flat file system, hierarchical database, relational database, or distributed database. Data for a group of events may be analyzed and/or summarized in various formats. Graphical and/or textual summary information may be displayed on the user interface and/or otherwise communicated to the user. For example, histograms, trend graphs, and/or other analytical tools or formats may be generated based on the logbook event entries. A logbook display may have the ability to display trends of the patient's apnea/hypopnea index, histograms of number of apneas/hypopneas and/or obstructive/central events per night, sleep stage diagram (shows the stage of sleep for each night), heart rate trend during the night, oxygen saturation trend during the night.

Figure 1C:
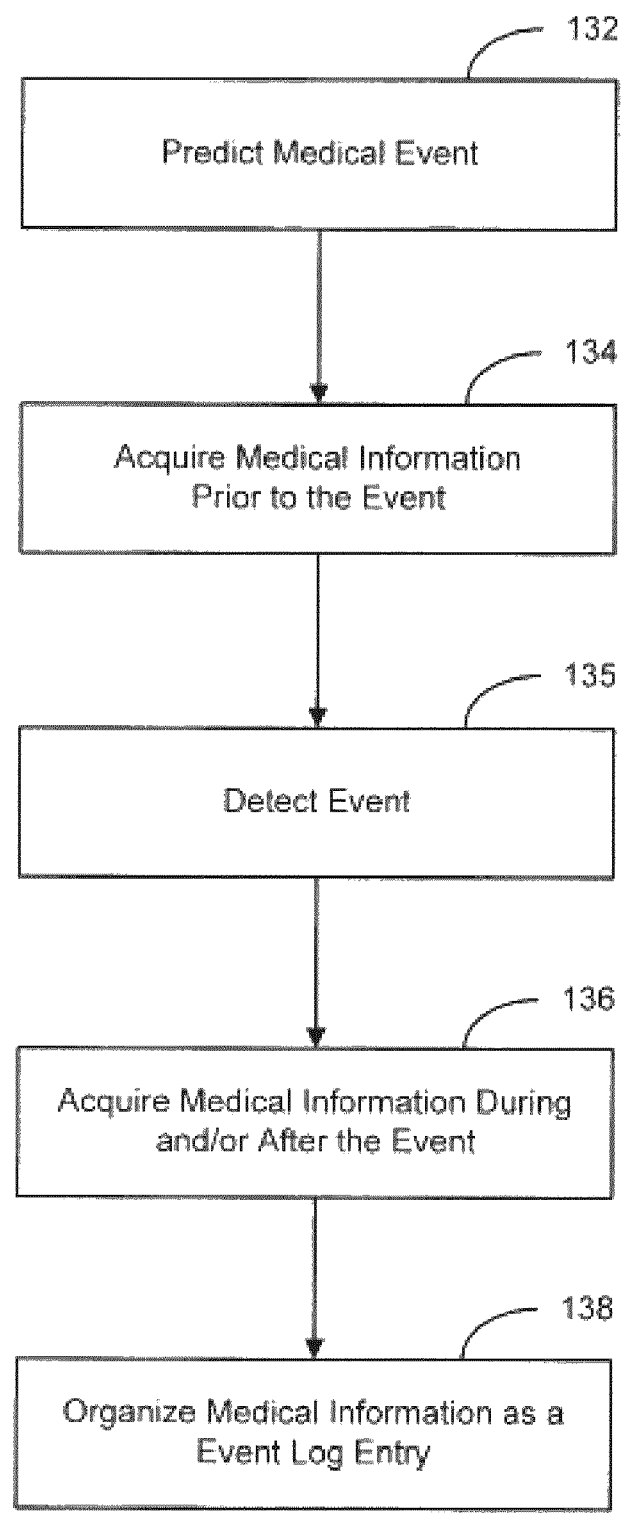

In various embodiments, collection of medical information may be initiated responsive to prediction of a medical event. In this scenario, information may be collected prior to the prediction of the medical event, prior to the detection of the medical event, during the event, and/or following the event. FIG. 1C is a flowchart illustrating an embodiment of the invention involving collecting medical information responsive to prediction and detection of a medical event. In this scenario, a medical event is predicted 132, initiating collection of information 134. Prior to the prediction, medical conditions affecting the patient may be monitored continuously or during discrete intervals and stored in a temporary buffer. Information contained in the temporary buffer represents information occurring before the prediction and may be collected for the medical event log entry. In addition, information may be collected after the prediction and before the detection of the event. If the event is detected 135, information may be collected during 136 and after the detected event. The collected information is organized 138 as an event log entry.

The approaches illustrated and described herein are generally presented in terms of a respiratory logbook system configured to organize medical information associated with respiratory events. Those skilled in the art will recognize that analogous approaches may be used to implement organization of respiratory information associated with medical events in a medical logbook system.

Figure 2:
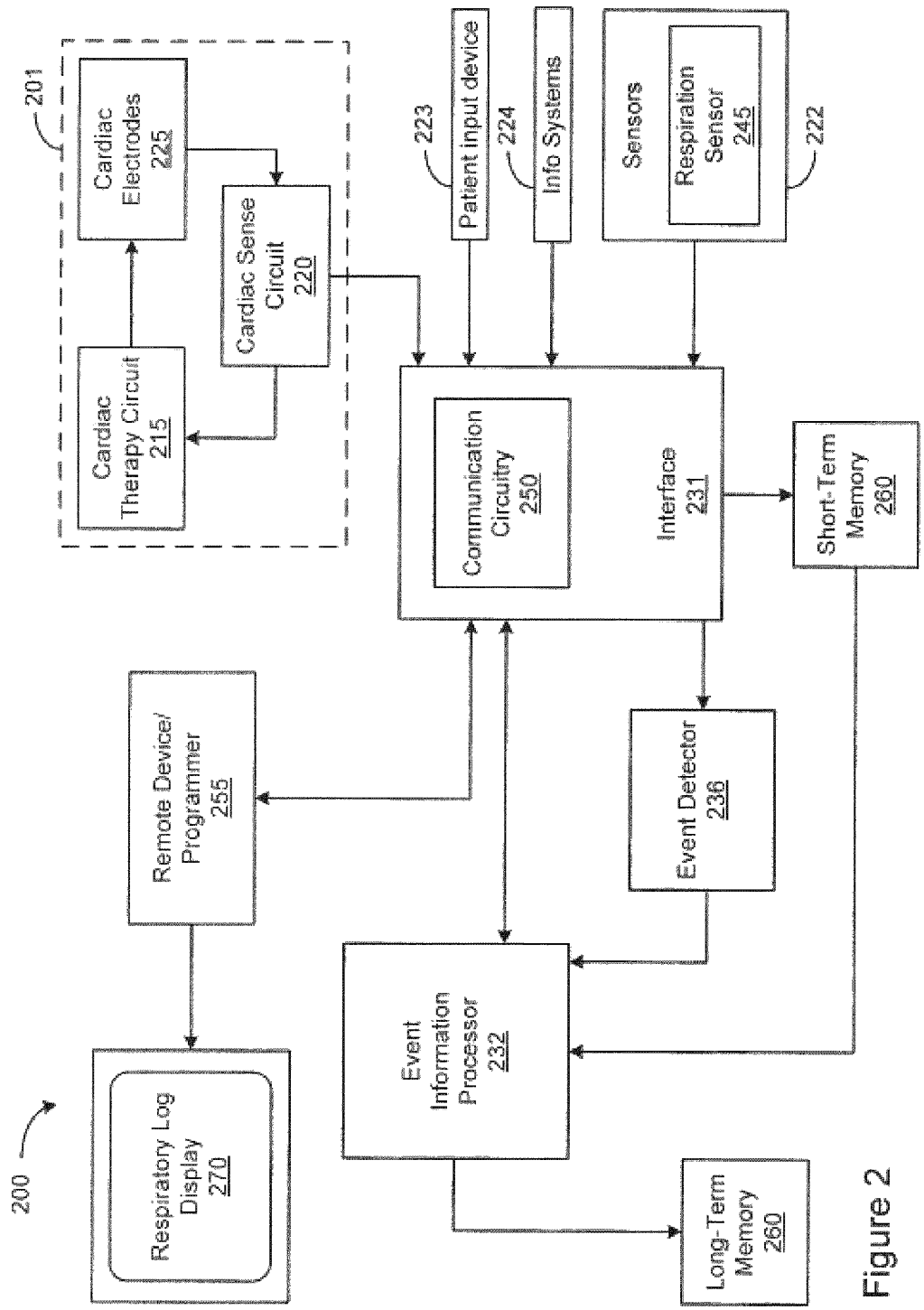
FIG. 2 is a block diagram of a respiratory logbook system in accordance with embodiments of the invention.

FIG. 2 is a block diagram of a logbook system 200 in accordance with embodiments of the invention. The respiratory logbook system 200 implements an event-driven method of collecting and organizing data related to events affecting patient respiration.

Various patient conditions may be monitored through sensors 222, patient input devices 223, and/or information systems 224. Data associated with patient conditions may be stored in short term memory 240. One or more of the patient conditions may be used by event detection circuitry 236 to detect or predict the occurrence of an event affecting respiration. Detection or prediction of an event affecting respiration initiates the long term storage of information associated with the event by the event information processor 232 into the long term memory 260. For example, the event information processor 232 may collect information supplied by one or more of the sensors 222, patient input devices 223, and information systems 224 before, during, and/or after the detection and/or prediction of the event. The collected information associated with each event is organized as a respiratory logbook entry in the respiratory logbook. The respiratory logbook, or portions thereof, may be stored in long term memory 260, transmitted to a remote device 255, and/or displayed on a display device 270.

The embodiment illustrated in FIG. 2 includes a respiration sensor 245 that senses a physiological condition modulated by patient respiration. In one embodiment, the respiration sensor may comprise a transthoracic impedance sensor. Other methods of sensing respiration are also possible. Such methods may include, for example, the use of patient-external respiratory bands, respiration flowmeter measurements, implantable or patient-external breath sound detection, blood oxygen levels, and/or other processes. The respiration sensor 245 may be used, for example, to acquire a respiration waveform before, during, and/or after an event affecting the patient respiration. The respiration waveform may be a component of the respiratory log entry for the event.

Information about various conditions affecting the patient and associated with the event may be acquired using sensors 222, patient input devices 223 and/or other information systems 224. The sensors 222 may comprise patient-internal and/or patient-external sensors coupled through leads or wirelessly to the interface 231 of the respiratory logbook system 200. The sensors may sense various physiological and/or non-physiological conditions affecting patient respiration or other physiological systems. The patient input device 223 allows the patient to input information relevant to conditions affecting the patient that may be useful in generating a respiratory event log. For example, the patient input device 223 may be particularly useful for acquiring information known to the patient, such as information related to patient smoking, drug use, recent exercise level, and/or other patient activities, perceptions and/or symptoms. The information provided by the patient-input device may include patient-known information relevant to the event affecting respiration that is not automatically sensed or detected by the respiratory logbook system 200.

The respiratory logbook system 200 may also include one or more information systems 224 such as a remote computing device and/or a network-based server. The event information processor 232 may access the information systems 224 to acquire information from databases and/or other information sources stored on or generated by the remote computing devices and/or servers. The information acquired from the information systems 224 may be recorded in the respiratory logbook along with other information relevant to the event affecting respiration. In one exemplary implementation, the respiratory logbook system 200 may access an internet connected air quality server to collect data related to environmental conditions, such as an ambient pollution index. In another implementation, the respiratory logbook system 200 may access the patient's medical history through a patient information server.

The sensors 222, patient input devices 223, and information systems 224 are coupled to other components of the respiratory logbook system 200 through interface circuitry 231. The interface 231 may include circuitry for energizing the sensors 222 and/or for detecting and/or processing signals generated by the sensors. The interface 231 may include, for example, driver circuitry, amplifiers, filters, sampling circuitry, and/or A/D converter circuitry for conditioning the signals generated by the sensors.

The interface 231 may also include circuitry 250 for communicating with the patient input device 223, information systems 224, a device programmer 255, an APM system (not shown), or other remote devices. Communication with the patient input device 223, information systems 224 and/or a remote device programmer 255 and/or other remote devices may be implemented using a wired connection or through a wireless communication link, such as a Bluetooth or other wireless link. The communication circuitry 250 may also provide the capability to wirelessly communicate with various sensors, including implantable, subcutaneous, cutaneous, and/or non-implanted sensors.

The respiratory logbook system 200 may optionally be implemented as a component of a medical device that includes a therapy system, such as a cardiac rhythm management system 201. The cardiac rhythm management system 201 may include cardiac electrodes 225 electrically coupled to the patient's heart. Cardiac signals sensed by cardiac sense circuitry 220 may be used in the detection and treatment of various anomalies of the heart rhythm. Anomalous heart rhythms may include, for example, a rhythm that is too slow (bradycardia), a heart rhythm that is too fast (tachycardia), and/or a heart rhythm that involves insufficiently synchronized contractions of the atria and/or ventricles, a symptom of congestive heart failure.

If an arrhythmia is detected by the cardiac rhythm management system, then a cardiac therapy circuit 215 may deliver cardiac therapy to the heart in the form of electrical stimulation pulses, such as pacing and/or cardioversion/defibrillation pulses. The cardiac signals and/or cardiac conditions, e.g., arrhythmia conditions, derived or detected through the use of the cardiac signals may be associated with an event affecting respiration. The cardiac information associated with the event may be acquired and organized by the respiratory logbook system 200.

Figure 3:
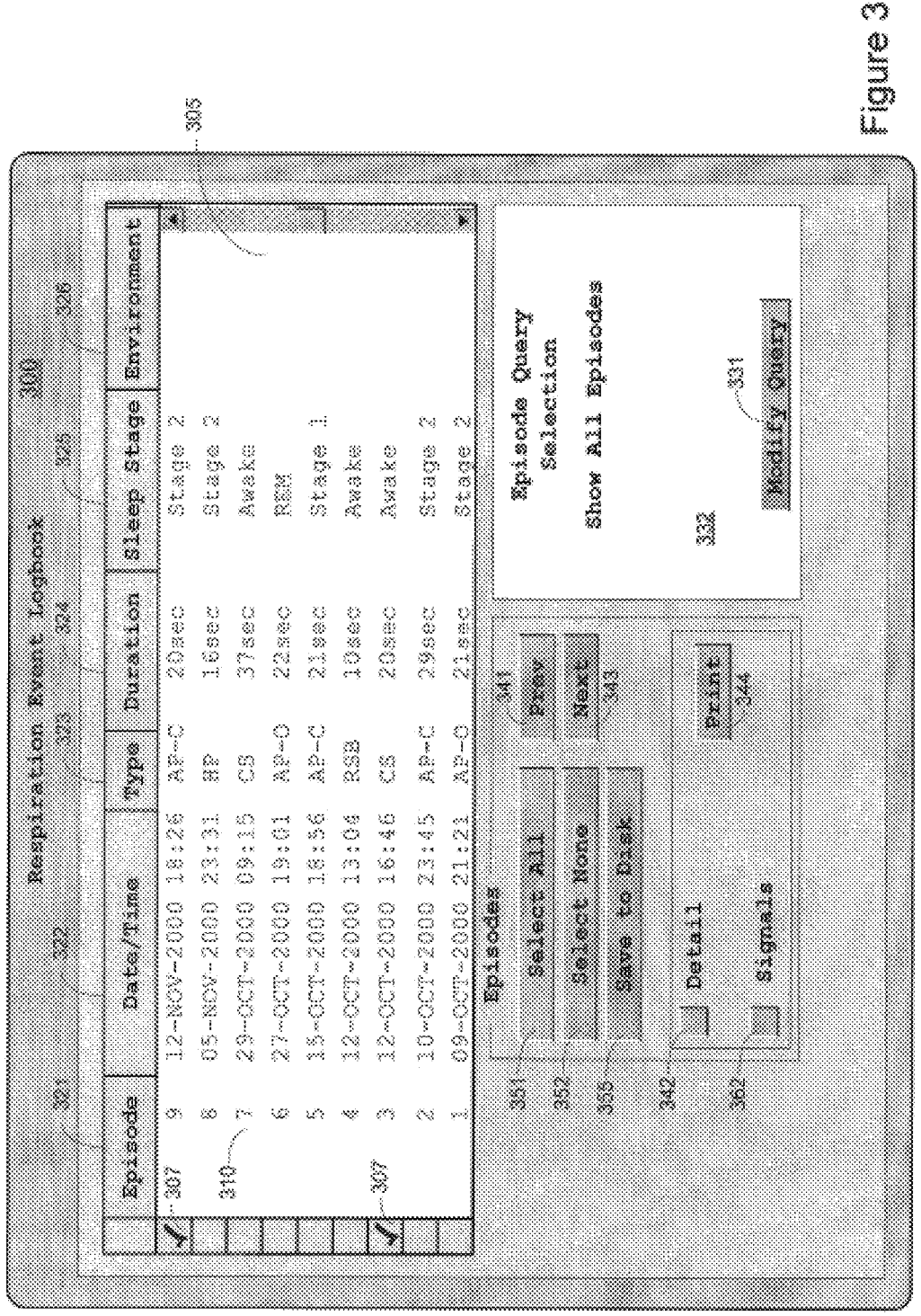
FIG. 3 illustrates an exemplary depiction of a user interface display that may be used with a respiratory logbook system in accordance with embodiments of the invention.

A user interface may be used to view and/or access the respiratory logbook information. FIG. 3 illustrates an exemplary depiction of a user interface display 300. An area 305 of the display may be used to provide textual or graphical information about respiratory events. As illustrated in FIG. 3, a menu 310 of respiratory events may be presented and may enable the user to access additional information related to the respiratory event. The menu 310 may provide a summary of parameters associated with the events contained in the respiratory logbook. As illustrated in FIG. 3, one or more summary parameter headings, such as episode number 321, date/time 322, type 323, duration 324, sleep stage 325, and/or environment 326, among other parameter headings, may be presented at the top of the menu 310 or in another convenient location. The summary parameter headings 321-326 may be programmable, and additional or alternative parameter headings to those depicted in FIG. 3 may be selected, for example.

The type parameter 323 may contain abbreviations for various respiratory events. For example AP-C and AP-O may abbreviate central and obstructive apneas respectively, HP abbreviates a hypopnea, CS abbreviates Cheyne-Stokes respiration and RSB abbreviates rapid-shallow breathing.

The respiratory events displayed as menu items in the menu 310 may be selected by a user according to episode number, date/time, duration, type, number, or by other criteria. The menu items may be selected for display based on various criteria ranges and/or thresholds. For example, in the example screen illustrated in FIG. 3, different groups of events selected as menu items may be selected by activating the modify query button 331. The modify query button 331 and other buttons illustrated on the display may be voice activated, activated through touching the display screen, or by operating a keyboard or pointing device, for example.

In one implementation, activation of the modify query button 331 initiates a dialog session that allows the user to select respiratory events to be presented in the menu according various criteria such as by date/time, duration, type, number, or by other criteria ranges or thresholds. In one example, the user may select all apnea events to be presented as menu items. In another example, the user may select all events that occurred between a first date and a second date. In yet another example, the user may select all events that occurred while the patient experienced certain environmental conditions, e.g., ambient temperature range and/or humidity range. In yet another example, the user may choose to select all events of the respiratory logbook. The selection criteria may be displayed in an episode query selection area 332 of the display. The episode query selection area 332 in the depiction of a respiratory logbook display shown in FIG. 3 indicates that all episodes have been selected to be displayed as menu items.

The menu 310 allows the user to choose respiratory events for which additional textual and/or graphical information is displayed. The additional information provides more detailed information about the selected events beyond the summary information presented in the menu 310. In the exemplary illustration depicted in FIG. 3, the selections are indicated by check marks 307 beside the selected respiratory events. For convenience, the display may include a select all button 351 and/or a select none button 352. Activation of the select all button 351 causes all events in the menu 310 to be selected. Activation of the select none button 352 causes all events in the menu 310 to be deselected.

Following selection of one or more episodes in the menu, activation of the detail button 342 causes detailed textual information associated with a selected event to be presented on the display screen. The detail information may be displayed in the area of the screen 305 previously occupied by the menu 310, for example. The user may scroll back and forth through the textual information for the one or more selected events using the prev button 341 and the next button 343. The textual information may be printed upon activation of the print button 344, or may be saved to a disk, or other storage medium, through activation of the save to disk button 355.

Graphical information associated with the selected events may be displayed upon activation of the signals button 362. In one implementation, a respiration waveform acquired during, before and/or after a selected event may be displayed in the area 305 of the display previously used for the menu 310. Waveforms of other parameters, e.g., cardiac rhythm, patient activity, may additionally or alternatively be displayed. In one implementation, a marked waveform may be displayed. For example, a marked respiration waveform may include the respiration waveform acquired before, during, and after the event, along with one or more symbols aligned with the respiration waveform to indicate the occurrence of one or more conditions. The symbol may provide a numerical value or a textual description associated with the respiration characteristic, e.g., average respiration rate, expiratory slope, etc. In one example, various characteristics of disordered breathing events including quantifiable characteristics, such as episode duration, blood oxygen saturation, disordered breathing type, and/or other detected characteristics may also be displayed along with the respiration waveform. A user may scroll through the waveforms associated with the selected events using the prev and next buttons 341, 343.

Figure 4:
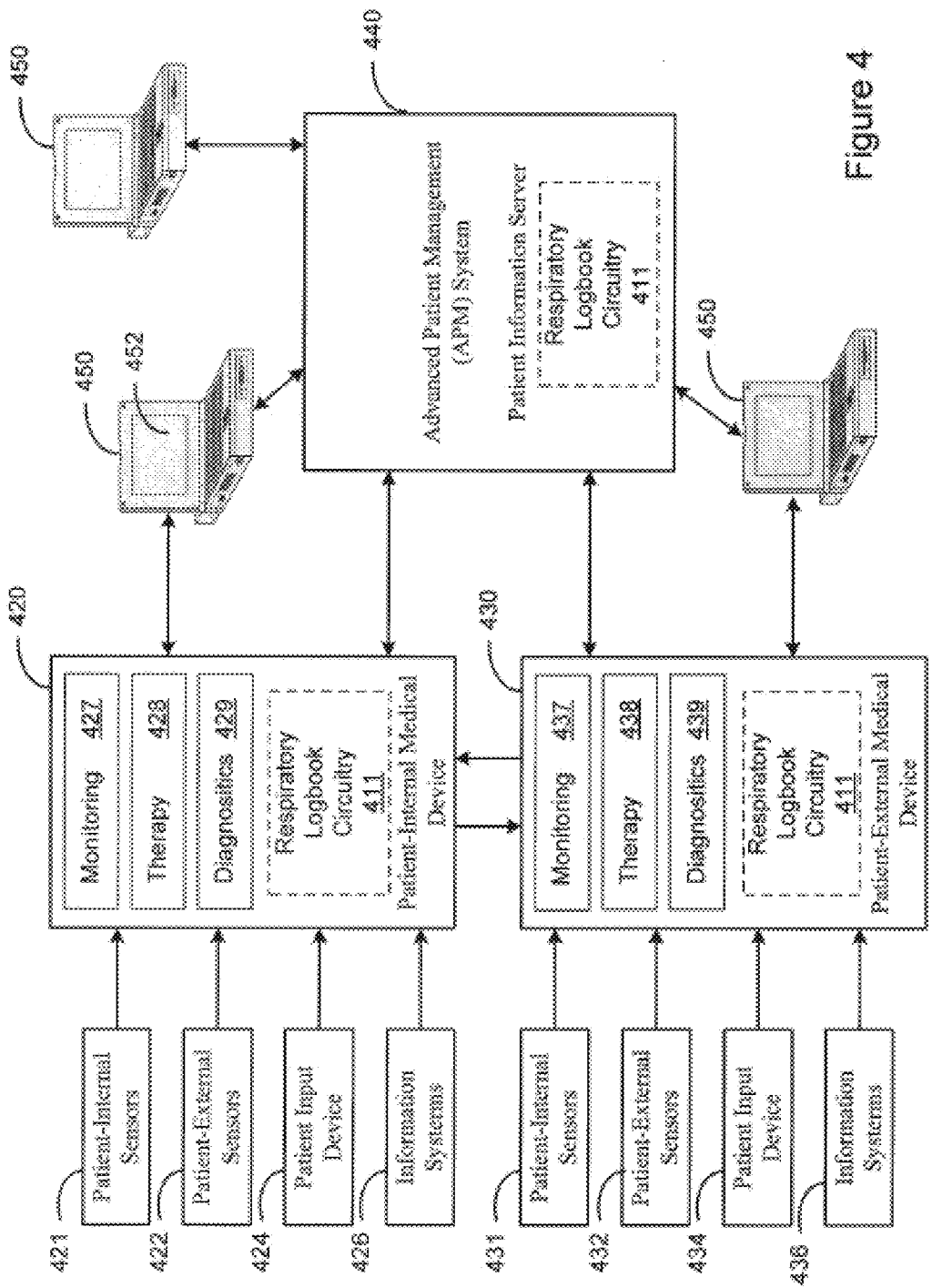
FIG. 4 is a block diagram of a medical system that may be used to implement a respiratory logbook system in accordance with embodiments of the invention.

FIG. 4 is a block diagram of a medical system that may be used to implement a respiratory logbook system in accordance with embodiments of the invention. The medical system may include, for example, one or more patient-internal medical devices 420 and one or more patient-external medical devices 430. Each of the patient-internal 420 and patient-external 430 medical devices may include one or more of a patient monitoring unit 427, 437, a diagnostics unit 429, 439, and/or a therapy unit 428, 438. Respiratory logbook circuitry 411, as described more fully in connection with FIG. 2 above, including an external device interface, event detector/predictor, event information processor and/or memory, for example, can be housed in a patient internal medical device 420, a patient external medical device 430, a remote system such as advanced patient medical (APM) system 440 or in any combination of the above-mentioned devices 420, 430, 440.

The patient-internal medical device 420 may be a fully or partially implantable device that performs monitoring, diagnosis, and/or therapy functions. The patient-external medical device 430 may perform monitoring, diagnosis and/or therapy functions external to the patient (i.e., not invasively implanted within the patient's body). The patient-external medical device 430 may be positioned on the patient, near the patient, or in any location external to the patient. It is understood that a portion of a patient-external medical device 430 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 420, 430 may be coupled to one or more sensors 421, 422, 431, 432, patient input devices 424, 434 and/or other information acquisition devices 426, 436. The sensors 421, 422, 431, 432, patient input devices 424, 434, and/or other information acquisition devices 426, 436 may be employed to detect conditions relevant to the monitoring, diagnostic, and/or therapeutic functions of the patient-internal and patient-external medical devices 420, 430.

The medical devices 420, 430 may each be coupled to one or more patient-internal sensors 421, 431 that are fully or partially implantable within the patient. The medical devices 420, 430 may also be coupled to patient-external sensors 422, 432 positioned on the patient, near the patient, or in a remote location with respect to the patient. The patient-internal 421, 431 and patient-external 422, 432 sensors may be used to sense conditions, such as physiological or environmental conditions, that affect the patient.

The patient-internal sensors 421 may be coupled to the patient-internal medical device 420 through implanted leads. In one example, an internal endocardial lead system is used to couple sensing electrodes to an implantable pacemaker or other cardiac rhythm management device. One or more of the patient-internal sensors 421, 431 may be equipped with transceiver circuitry to support wireless communication between the one or more patient-internal sensors 421, 431 and the patient-internal medical device 420 and/or the patient-external medical device 430.

The patient-external sensors 422, 432 may be coupled to the patient-internal medical device 410 and/or the patient-external medical device 420 through leads or through wireless connections. Patient-external sensors 422 preferably communicate with the patient-internal medical device 420 wirelessly. Patient-external sensors 432 may be coupled to the patient-external medical device 430 through leads or through a wireless link.

The medical devices 420, 430 may be coupled to one or more patient-input devices 424, 434. The patient-input devices 424, 434 facilitate manual transfer of information to the medical devices 420, 430 by the patient. The patient input devices 424, 434 may be particularly useful for inputting information concerning patient perceptions, such as how well the patient feels, and patient-known information such as patient smoking, drug use, or other activities that are not automatically sensed or detected by the medical devices 420, 430. In one implementation, a device programmer may be used to facilitate patient input to a medical device 420, 430.

The medical devices 420, 430 may be connected to one or more information systems 426, 436, for example, a database that stores information useful in connection with the monitoring, diagnostic, or therapy functions of the medical devices 420, 430. In one implementation, one or more of the medical devices 420, 430 may be coupled through a network to an information system server that provides information about environmental conditions affecting the patient, e.g., the pollution index for the patient's location.

In one embodiment, the patient-internal medical device 420 and the patient-external medical device 430 may communicate through a wireless link between the medical devices 420, 430. For example, the patient-internal and patient-external devices 420, 430 may be coupled through a short-range radio link, such as Bluetooth or a wireless link. The communications link may facilitate uni-directional or bi-directional communication between the patient-internal 420 and patient-external 430 medical devices. Data and/or control signals may be transmitted between the patient-internal 420 and patient-external 430 medical devices to coordinate the functions of the medical devices 420, 430.

In one embodiment, the patient-internal and patient-external medical devices 420, 430 may be used within the structure of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

The patient-internal medical device 420 and the patient-external medical device 430 may be coupled through a wireless or wired communications link to a patient information server that is part of an advanced patient management system 440. The APM patient information server 440 may be used to download and store data collected by the patient-internal and patient-external medical devices 420, 430.

The data stored on the APM patient information server 440 may be accessible by the patient and the patient's physician through terminals 450, e.g., remote computers located in the patient's home or the physician's office. The APM patient information server 440 may be used to communicate to one or more of the patient-internal and patient-external medical devices 420, 430 to effect remote control of the monitoring, diagnosis, and/or therapy functions of the medical devices 420, 430.

In one scenario, the patient's physician may access patient data transmitted from the medical devices 420, 430 to the APM patient information server 440. After evaluation of the patient data, the patient's physician may communicate with one or more of the patient-internal or patient-external devices 420, 430 through the APM system 440 to initiate, terminate, or modify the monitoring, diagnostic, and/or therapy functions of the patient-internal and/or patient-external medical systems 420, 430. Systems and methods involving advanced patient management techniques are further described in the previously incorporated U.S. Pat. Nos. 6,336,903, 6,312,378, 6,270,457, and 6,398,728.

In one scenario, the patient-internal and patient-external medical devices 420, 430 may not communicate directly with each other, but may communicate indirectly through the APM system 440. In this embodiment, the APM system 440 may operate as an intermediary between two or more of the medical devices 420, 430. For example, data and/or control information may be transferred from one of the medical devices 420, 430 to the APM system 440. The APM system 440 may transfer the data and/or control information to another of the medical devices 420, 430.

As previously indicated, respiratory logbook circuitry 411, including an external device interface, event detector/predictor, event information processor and memory, for example, can be housed in a patient internal medical device 420, a patient external medical device 430, an advanced patient medical (APM) system 440 or in any combination of the above-mentioned devices. For explanatory purposes, in the following discussion, the respiratory logbook circuitry 411 is described as being housed within the patient internal medical device 420. As previously discussed, the patient internal medical device 420 is coupled to various sensors, 421, 422, patient input devices 424, and/or other information systems 426. These sensing and detection devices may be used to detect conditions relevant to events affecting respiration. One or more patient input devices 424 allow the patient to enter information associated with the events into the medical device 420. Further, a variety of information systems 426 may be accessible by the patient-internal medical device 420, including, for example, network or internet-based information systems. The information systems 426 may provide event-related information such as local pollution levels, local temperature, humidity, etc. For example, the conditions associated with events affecting respiration may be any of the conditions referred to in Tables 1-3, or other conditions.

In accordance with various embodiments of the invention, the respiratory logbook circuitry 411 may comprise circuitry configured to evaluate one or more patient conditions to detect or predict the occurrence of an event affecting patient respiration. In response to the detection or prediction of such an event, the respiratory logbook circuitry initiates the collection of information related to the event. In one scenario, the respiratory logbook circuitry may initiate collection of information from sensors 421, 431, 422, 432 or other input devices 424, 434, 426, 436 coupled to any combination of the patient internal medical device, 420 patient external medical device 430 and a remote device, such as the APM server 440. The respiratory logbook circuitry may initiate collection of information associated with any of the patient conditions listed in Tables 1-3.

Information associated with the event affecting respiration may be acquired before, during and/or after the respiratory event. Information may be acquired for a time period beginning a short time, e.g., up to about 5 minutes, prior to the prediction and/or detection of a respiratory event and/or ending a short time, e.g., up to about 2 minutes, following the termination of the respiratory event. In various embodiments of the invention, acquired information related to the event affecting respiration may be immediately transmitted to a separate computing device 430, 440, 450, the acquired information may be stored in the patient-internal device 420. The information may be organized and displayed on a display unit 452 as discussed in connection with FIG. 3.

The patient-internal sensors 421, 431, patient-external sensors 422, 432, patient input devices 424, 434, and/or information systems 426, 436 may be used to acquire a variety of information related to respiratory logbook events. The acquired information may include both physiological and non-physiological contextual conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Contextual conditions generally encompass non-physiological, patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. Pat. No. 7,400,928, which is incorporated by reference herein in its entirety.

Table 1 provides a list of representative patient conditions that may be used in connection with a respiratory logbook in accordance with embodiments of the invention. Table 1 presents representative physiological and non-physiological patient conditions that may be acquired and used in connection with a respiratory logbook. Table 1 also presents illustrative sensing methods that may be employed to sense the conditions. It will be appreciated that information and detection methods other than those provided in Table 1 may be used in connection with a respiratory logbook and are considered to be within the scope of the invention.

TABLE 1

| Condition Type | | Condition | Sensor type or Detection method |
|---|---|---|---|
| Physiological | Cardiovascular System | Heart rate<br>Heart rate variability<br>QT interval | EGM, ECG |
| | | Ventricular filling pressure | Intracardiac pressure sensor |
| | | Blood pressure | Blood pressure sensor |
| | Respiratory System | Snoring | Accelerometer<br>Microphone |
| | | Respiration pattern<br>(Tidal volume Minute<br>ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation<br>O2 saturation<br>Blood alcohol content<br>Adrenalin<br>Brain Natriuretic Peptide (BNP)<br>C-Reactive Protein<br>Drug/Medication/Tobacco use | Blood analysis |
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Date | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history<br>Age<br>Recent exercise<br>Weight<br>Gender<br>Body mass index<br>Neck size<br>Emotional state<br>Psychological history<br>Daytime sleepiness<br>Patient perception of sleep quality<br>Drug, alcohol, nicotine use | Patient input |

As previously mentioned, long term storage of respiratory logbook information may be initiated by detection or prediction of various types of events affecting the respiration of the patient. The triggering event may comprise, for example, a disordered breathing event, a cardiac arrhythmia episode, an event related to a pulmonary disease or disorder such as asthma, pulmonary edema, chronic obstructive pulmonary disease, and/or pleural effusion, an episode of coughing and/or other breathing irregularities, or an event related to the normal activity of the patient, such as sleep or exercise, among other events. The event may also be triggered by the patient using, for example, the patient input device 424, 434.

Detection of various pulmonary diseases/disorders may initiate long term storage of data for a respiratory logbook entry. Pulmonary diseases/disorders may be organized into broad categories encompassing disorders of breathing rhythm and non-rhythm pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm related are referred to herein as non-rhythm pulmonary diseases and may include obstructive pulmonary diseases, restrictive pulmonary diseases, infectious pulmonary diseases, pulmonary vasculature disorders, and pleural cavity disorders, for example.

In various embodiments of the invention, acquisition of information may be triggered by detection of a presence of a non-rhythm related pulmonary disease/disorder. Detection of a presence of the pulmonary disease/disorder may be based on a predetermined level of physiological changes and/or disease symptoms associated with the disease or disorder. The presence of various pulmonary diseases that may trigger acquisition of data may include, for example, obstructive pulmonary diseases (e.g., chronic bronchitis, emphysema, asthma), restrictive pulmonary diseases (e.g., sarcoidosis, pulmonary fibrosis, pneumoconiosis), infections pulmonary diseases (e.g., bronchitis, pneumonia, bronchiolitis, tuberculosis, and bronchiectasis), pulmonary vasculature diseases (e.g., pulmonary hypertension, pulmonary edema, pulmonary embolism, atalectasis), and diseases of the pleural cavity (e.g., pleural effusion, pneumothorax, and hemothorax).

In accordance with various embodiments of the invention, the presence of a non-rhythm pulmonary disease may be assessed by evaluating conditions indicative of the non-rhythm pulmonary disease. In one example, the presence of a non-rhythm pulmonary disease may be assessed by comparing conditions indicative of physiological changes or symptoms caused by the disease to threshold criteria. If the conditions indicative of physiological changes or symptoms caused by the disease are consistent with threshold levels, the system may determine that the non-rhythm pulmonary disease or disorder is present.

In another example, assessment of disease presence may be based on relative changes in one or more conditions indicative of physiological changes or symptoms caused by the disease. For example, diagnosis of a non-rhythm pulmonary disease may be effected by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, the non-rhythm pulmonary disease or disorder may be present.

In a further example, the threshold criteria may involve relationships between the conditions indicative of physiological changes or symptoms caused by the disease. The presence of a non-rhythm pulmonary disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the non-rhythm pulmonary disease or disorder may be present.

In another implementation, detection of a rhythm related pulmonary event, e.g., a disordered breathing event, triggers the acquisition of information associated with respiration. A disordered breathing event may be detected by sensing and analyzing various conditions indicative of disordered breathing. Table 2 presents examples of how a representative subset of the physiological and non-physiological (contextual) conditions provided in Table 1 may be used in connection with disordered breathing detection.

TABLE 2

| Condition Type | Condition | Examples of how condition may be used in disordered breathing detection |
|---|---|---|
| Physiological | Heart rate | Decrease in heart rate may indicate disordered breathing episode. Increase in heart rate may indicate autonomic arousal from a disordered breathing episode. Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. Snoring indicates the patient is asleep. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | CO2 | Low CO2 levels initiate central apnea. May be used to predict central apnea risk. |
| | O2 | O2 desaturation occurs during severe apnea/hypopnea episodes. May be used to evaluate presence and severity of sleep disordered breathing event. |
| | Blood alcohol content | Alcohol tends to increase incidence of snoring & obstructive apnea. |
| | Adrenalin | End of apnea associated with a spike in blood adrenaline. |
| | Brain Natriuretic Peptide (BNP) | A marker of heart failure status, which is associated with Cheyne-Stokes Respiration |
| | C-Reactive Protein | A measure of inflammation that may be related to apnea. |
| | Drug/ Medication/ Tobacco use | These substances may affect the incidence of both central & obstructive apnea. |
| | Muscle atonia | Muscle atonia may be used to discriminate REM from non-REM sleep. |
| | Eye movement | Eye movement may be used to detect REM and non-REM sleep. |
| Non-physiological/ Contextual | Temperature | Ambient temperature may be a condition predisposing the patient to episodes of disordered breathing and may be useful in disordered breathing detection. |

TABLE 2-continued

| Condition Type | Condition | Examples of how condition may be used in disordered breathing detection |
|---|---|---|
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

The acquisition of information may be triggered by a prediction that a disordered breathing event is likely to occur. In this implementation, an occurrence of disordered breathing may be predicted based on one or more sensed conditions, such one or more of the physiological and/or non-physiological conditions listed in Table 1. The conditions listed in Table 1 may serve a variety of purposes in predicting disordered breathing. For example, a first subset of the conditions listed in Table 1 may comprise conditions predisposing the patient to disordered breathing. Another subset, possibly overlapping the first subset, may comprise precursor conditions indicating an imminent occurrence of a disordered breathing event. Another subset of the conditions may be employed to verify that the predicted disordered breathing event occurred and/or to classify the disordered breathing episode as to origin, e.g., central or obstructive, and/or as to type, e.g., apnea, hypopnea, Cheyne-Stokes Respiration (CSR). Table 3 provides further examples of how physiological and/or contextual conditions may be used in disordered breathing prediction.

TABLE 3

| Condition | Examples of how condition is used in disordered breathing prediction |
|---|---|
| Heart rate | Decrease in heart rate may indicate disordered breathing episode. |
| | Decrease in heart rate may indicate the patient is asleep. |
| | Increase in heart rate may indicate autonomic arousal from disordered breathing. |
| Heart rate variability | May be used to determine sleep state |
| Ventricular filling pressure | May be used to identify/predict pulmonary congestion associated with respiratory disturbance. |
| Blood pressure | Swings in on-line blood pressure measures are associated with apnea. |
| Snoring | Snoring is associated with a higher incidence of obstructive sleep apnea and may be used to detect disordered breathing. |
| Respiration signals/ respiration patterns | Respiration patterns may be used to detect disordered breathing episodes. |
| | Respiration patterns may be used to determine the type of disordered breathing. |
| | Respiration patterns may be used to detect that the patient is asleep. |
| | Hyperventilation may be used to predict disordered breathing. |
| | Previous episodes of disordered breathing may be used to predict further episodes. |

TABLE 3-continued

| Condition | Examples of how condition is used in disordered breathing prediction |
|---|---|
| | One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/ hypopnea episodes. |
| Blood alcohol content | Alcohol tends to increase incidence of snoring & obstructive apnea. |
| Adrenalin | End of apnea associated with a spike in blood adrenaline. |
| BNP | A marker of heart failure status, which is associated with Cheyne-Stokes Respiration |
| C-Reactive Protein | A measure of inflammation that may be related to apnea. |
| Drug/Medication/ Tobacco use | These substances may affect incidence of both central & obstructive apnea. |
| Muscle atonia | Muscle atonia may be used to detect REM and non-REM sleep. |
| Eye movement | Eye movement may be used to detect REM and non-REM sleep. |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep. Posture may be a condition predisposing the patient to episodes of disordered breathing. |
| Activity | Patient activity may be used in relation to sleep detection. |
| Sleep stage | NREM sleep is associated with a higher incidence of DB episodes |
| Location | Patient location may used to determine if the patient is in bed as a part of sleep detection. |
| Altitude | Lower oxygen concentration associated with high altitudes predisposes patients to more central apnea |

Detection or prediction of disordered breathing may involve comparing one condition or multiple conditions to one or more thresholds or other indices indicative or predictive of disordered breathing. A threshold or other index indicative or predictive of disordered breathing may comprise a predetermined level of a particular condition, e.g., blood oxygen level less than a predetermined amount. A threshold or other index indicative or predictive of disordered breathing may involve a change in a level of a particular condition, e.g., heart rate decreasing from a sleep rate to a lower rate within a predetermined time interval.

In one approach, the relationships between the conditions may be indicative or predictive of disordered breathing. In this embodiment, disordered breathing detection or prediction may be based on the existence and relative values associated with two or more conditions. For example, if condition A is present at a level of x, then condition B must also be present at a level of f(x) before disordered breathing is detection or predicted.

The thresholds and/or relationships indicative or predictive of disordered breathing may be highly patient specific. The thresholds and/or relationships indicative of disordered breathing may be determined on a case-by-case basis by monitoring conditions affecting the patient and monitoring disordered breathing episodes. The analysis may involve determining levels of the monitored conditions and/or relationships between the monitored conditions associated, e.g., statistically correlated, with disordered breathing episodes. The thresholds and/or relationships used in disordered breathing detection or prediction may be updated periodically to track changes in the patient's response to disordered breathing.

In various implementations, disordered breathing events may be detected through analysis of the patient's respiration patterns. Methods and systems of disordered breathing detection based on respiration patterns that may be utilized in a respiratory logbook system are further described in commonly owned U.S. Pat. No. 7,252,640, which is incorporated herein by reference.

Prediction of disordered breathing may involve analysis of conditions predisposing the patient to disordered breathing. Additionally, or alternatively, prediction of disordered breathing may be based on the detection of precursor conditions that indicate a likelihood that one or more episodes of disordered breathing will occur during the next time period, such as over the course of the night. Methods and systems for predicting disordered breathing that may be implemented in a respiratory logbook system are further described in commonly owned U.S. Pat. No. 7,396,333, which is incorporated herein by reference.

Respiratory events may be more likely to occur during sleep. For example, episodes of disordered breathing can occur when the patient is awake, however, most disordered breathing events occur during sleep. The onset and termination or sleep, sleep state, and/or stage of sleep may comprise events that initiate acquisition of information organized in a respiratory logbook. Methods and systems for detecting sleep that may be implemented in the context of a respiratory logbook are described in commonly owned U.S. Pat. No. 7,189,204, which is incorporated herein by reference.

Methods and systems for detecting REM sleep and/or other sleep states are described in commonly owned U.S. Pat. No. 8,192,376, "Sleep State Classification", which is incorporated herein by reference.

Information collected in accordance with the invention may involve information related to sleep and/or sleep quality. Methods and systems related to collection, assessment, and organization of sleep-related information are described in commonly owned U.S. Pat. Nos. 8,002,553 and 7,572,225, and U.S. Publication No. 2005/0076908, all of which are incorporated herein by reference.

Figure 5:
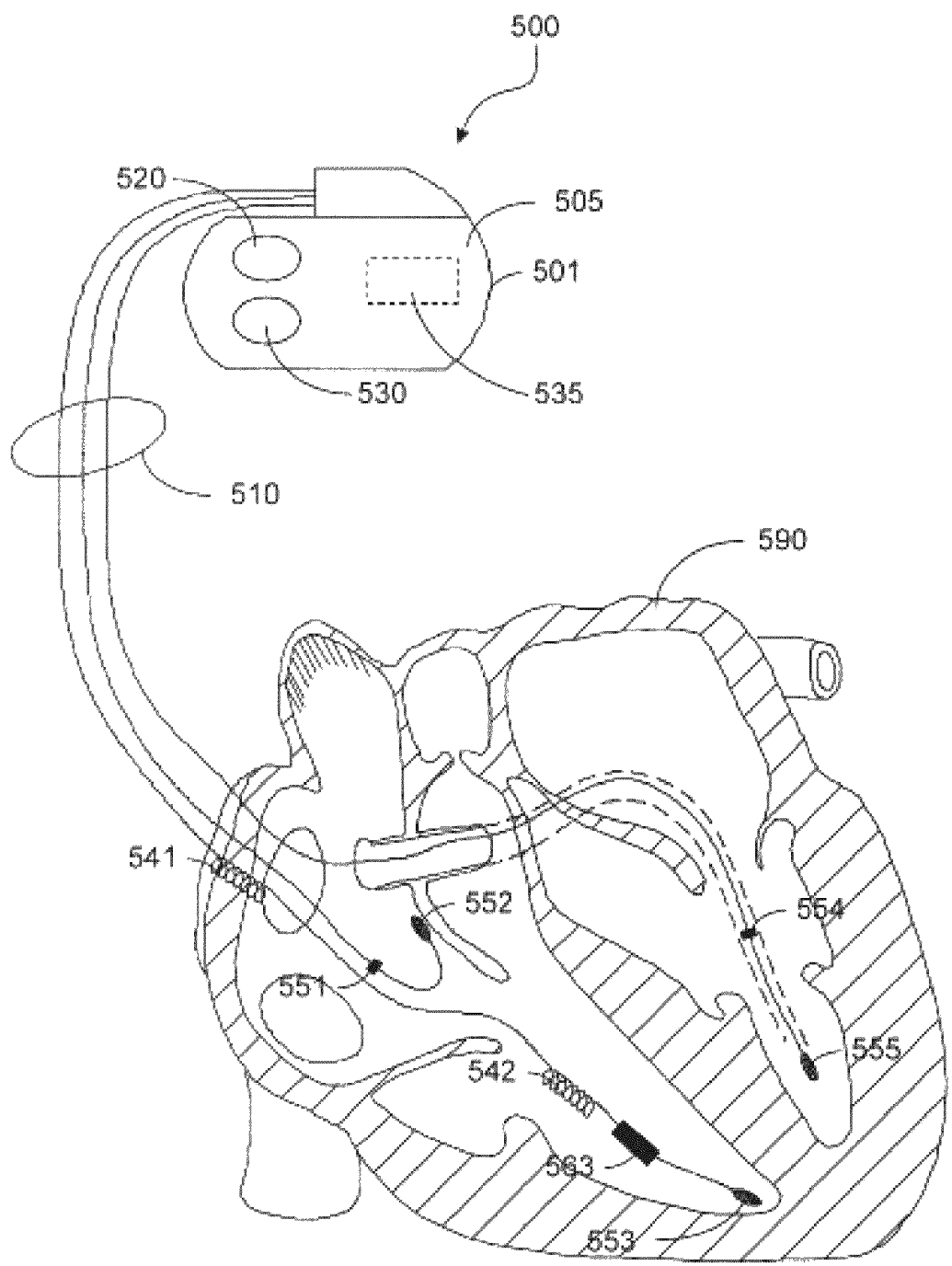
FIG. 5 is a partial view of an implantable device that may include circuitry for implementing a respiratory logbook in accordance with embodiments of the invention.

FIG. 5 is a partial view of an implantable device that may include circuitry for implementing a respiratory logbook in accordance with embodiments of the invention. In this example, the implantable device comprises a cardiac rhythm management device (CRM) 500 including an implantable pulse generator 505 electrically and physically coupled to an intracardiac lead system 510. The respiratory logbook system may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 510 are inserted into the patient's heart 590. The intracardiac lead system 510 includes one or more electrodes configured to sense electrical cardiac activity of the heart, deliver electrical stimulation to the heart, sense the patient's transthoracic impedance, and/or sense other physiological parameters, e,g, cardiac chamber pressure or temperature. Portions of the housing 501 of the pulse generator 505 may optionally serve as a can electrode.

Communications circuitry is disposed within the housing 501 for facilitating communication between the pulse generator 505 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 505 may optionally incorporate a motion detector 520 that may be used to sense various respiration-related conditions. For example, the motion detector 520 may be optionally configured to sense snoring, activity level, and/or chest wall movements associated with respiratory effort, for example. The motion detector 520 may be implemented as an accelerometer positioned in or on the housing 501 of the pulse generator 505. If the motion sensor is implemented as an accelerometer, the motion sensor may also provide respiratory, e.g. rales, coughing, and cardiac, e.g. S1-S4 heart sounds, murmurs, and other acoustic information.

The lead system 510 of the CRM 500 may incorporate one or more transthoracic impedance sensors that may be used to acquire the patient's respiration waveform, or other respiration-related information. The transthoracic impedance sensor may include, for example, one or more intracardiac electrodes 541, 542, 551-555, 563 positioned in one or more chambers of the heart 590. The intracardiac electrodes 541, 542, 551-555, 563 may be coupled to impedance drive/sense circuitry 530 positioned within the housing of the pulse generator 505.

In one implementation, impedance drive/sense circuitry 530 generates a current that flows through the tissue between an impedance drive electrode 551 and a can electrode on the housing 501 of the pulse generator 505. The voltage at an impedance sense electrode 552 relative to the can electrode changes as the patient's transthoracic impedance changes. The voltage signal developed between the impedance sense electrode 552 and the can electrode is detected by the impedance sense circuitry 530. Other locations and/or combinations of impedance sense and drive electrodes are also possible.

Figure 6:
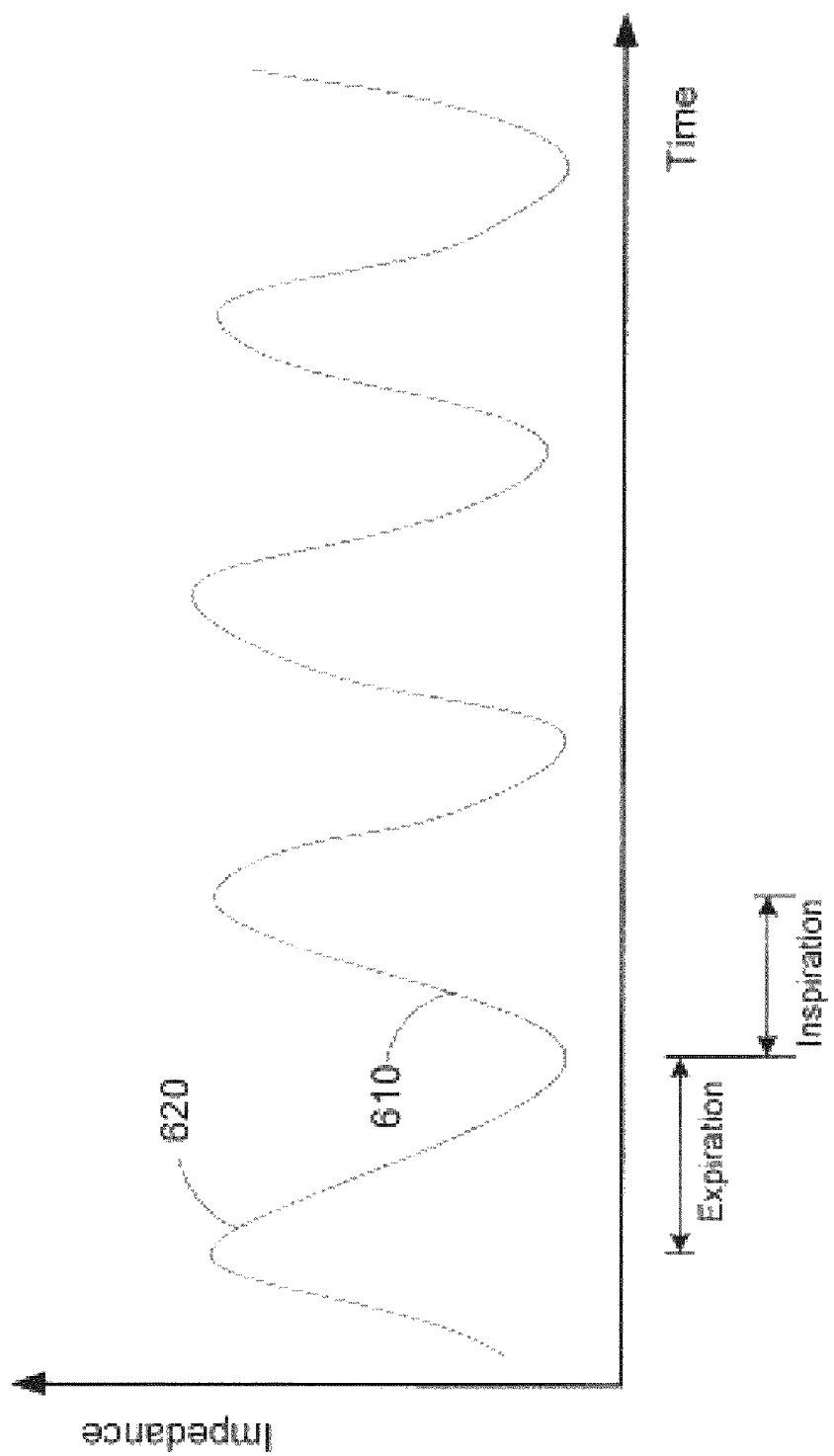
FIG. 6 is a graph illustrating a respiration waveform that may be acquired and organized as a portion of a respiratory log entry in accordance with embodiments of the invention.

The voltage signal developed at the impedance sense electrode 552, illustrated in FIG. 6, is proportional to the patient's transthoracic impedance and represents the patient's respiration waveform. The transthoracic impedance increases during respiratory inspiration 610 and decreases during respiratory expiration 620. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration—expiration cycles without substantial interruptions, as indicated in FIG. 6.

Returning to FIG. 5, the lead system 510 may include one or more cardiac pace/sense electrodes 551-555 positioned in, on, or about one or more heart chambers for sensing electrical signals from the patient's heart 590 and/or delivering pacing pulses to the heart 590. The intracardiac sense/pace electrodes 551-555, such as those illustrated in FIG. 5, may be used to sense and/or pace one or more chambers of the heart, including the left ventricle, the right ventricle, the left atrium and/or the right atrium. The lead system 510 may include one or more defibrillation electrodes 541, 542 for delivering defibrillation/cardioversion shocks to the heart.

The pulse generator 505 may include circuitry for detecting cardiac arrhythmias and/or for controlling pacing or defibrillation therapy in the form of electrical stimulation pulses or shocks delivered to the heart through the lead system 510. Circuitry for implementing a respiratory logbook 535, including interface circuitry, an event detector, an event processor, and/or memory circuitry, as described in connection with the FIG. 2, may be housed within the pulse generator 505. The respiratory logbook circuitry may be coupled to various sensors, patient input devices, and/or information systems through leads or through wireless communication links.

Figure 7:
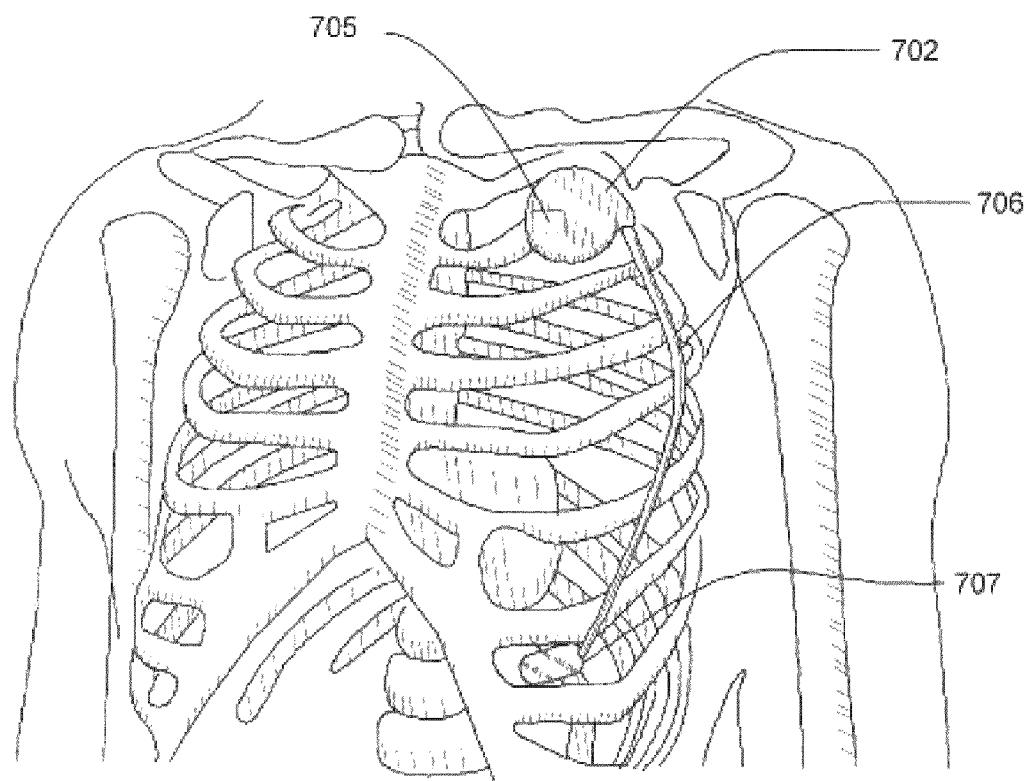
FIG. 7 is a diagram illustrating an implantable transthoracic cardiac device that may be used in connection with acquiring and organizing data for a respiratory logbook in accordance with embodiments of the invention.

FIG. 7 is a diagram illustrating an implantable transthoracic cardiac device that may be used in connection with acquiring and organizing data for a respiratory logbook in accordance with embodiments of the invention. The implantable device illustrated in FIG. 7 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a respiratory logbook system may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transveous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 7, a subcutaneous electrode assembly 707 can be positioned under the skin in the chest region and situated distal from the housing 702. The subcutaneous and, if applicable, housing electrode(s) can be positioned about the heart at various locations and orientations, such as at various anterior and/or posterior locations relative to the heart. The subcutaneous electrode assembly 707 is coupled to circuitry within the housing 702 via a lead assembly 706. One or more conductors (e.g., coils or cables) are provided within the lead assembly 706 and electrically couple the subcutaneous electrode assembly 707 with circuitry in the housing 702. One or more sense, sense/pace or defibrillation electrodes can be situated on the elongated structure of the electrode support, the housing 702, and/or the distal electrode assembly (shown as subcutaneous electrode assembly 707 in the configuration shown in FIG. 7).

It is noted that the electrode and the lead assemblies 707, 706 can be configured to assume a variety of shapes. For example, the lead assembly 706 can have a wedge, chevron, flattened oval, or a ribbon shape, and the subcutaneous electrode assembly 707 can comprise a number of spaced electrodes, such as an array or band of electrodes. Moreover, two or more subcutaneous electrode assemblies 707 can be mounted to multiple electrode support assemblies 706 to achieve a desired spaced relationship amongst subcutaneous electrode assemblies 707.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; 5,916,243; and 7,570,997; and commonly owned U.S. Patent Application Publication Nos. 2004/0230229; 2004/0230230; and 2004/0215240; and U.S. Patent Application Ser. No. 60/462,272, filed Apr. 11, 2003; all of which are incorporated herein by reference.

The housing of the ITCS device may incorporate components of a respiratory logbook system 705, including a memory, interface, event processor and/or event detector circuitry. The respiratory logbook circuitry may be coupled to one or more sensors, patient input devices, and/or information systems as described in connection with FIG. 2.

In one implementation, the ITCS device may include an impedance sensor configured to sense the patient's transthoracic impedance. The impedance sensor may include the impedance drive/sense circuitry incorporated with the housing 702 of the ITCS device and coupled to impedance electrodes positioned on the can or at other locations of the ITCS device, such as on the subcutaneous electrode assembly 707 and/or lead assembly 706. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 702 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

FIG. 8 is a block diagram illustrating a medical system 800 including a patient-internal device 810 that cooperates with a patient-external device 820 to acquire and organize information in a respiratory logbook in accordance with embodiments of the invention. In this example, the respiratory logbook is displayed on a display device 860 coupled to the patient-external device 820. Alternatively, the display device 860 could be coupled to the patient-internal device 810.

In one embodiment, the patient-internal device 810 may comprise, for example, an implantable cardiac rhythm management system (CRM) such as a pacemaker, defibrillator, cardiac resynchronizer, or the like. In another embodiment, the patient-internal device 810 may comprise, for example, an implantable transthoracic cardiac sensing and/or stimulation device (ITCS) as described in connection with FIG. 7. The patient-external device 820 may comprise an external breathing therapy device such as a continuous positive airway pressure device (CPAP), bi-level positive airway pressure device (bi-PAP) or other positive airway pressure device, generically referred to herein as xPAP devices.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any device using forms of positive airway pressure (and negative pressure when necessary), whether continuous or otherwise.

An xPAP device 820 develops a positive air pressure that is delivered to the patient's airway through tubing 832 and mask 854 connected to the xPAP device 820. Positive airway pressure devices are often used to treat disordered breathing. In one configuration, for example, the positive airway pressure provided by the xPAP device 820 acts as a pneumatic splint keeping the patient's airway open and reducing the severity and/or number of occurrences of disordered breathing due to airway obstruction. In addition to delivering breathing therapy, the xPAP device 820 may provide a number of monitoring and/or diagnostic functions in relation to the respiratory system. For example, the xPAP device 820 may sense respiration using an oxygen sensor, a microphone, a flow meter, and/or other respiration sensing methods.

Components used in connection with acquiring and organizing respiratory logbook information may be implemented by the patient-internal CRM 810 device, by the patient-external xPAP 820 device, or by both devices. Further, the CRM and the xPAP devices may be coupled to a remote computing device such as a patient management server using wireless or wired link.

The CRM 810 may provide a first set of monitoring, diagnostic, and/or therapeutic functions to the patient. The xPAP device 820 may provide a second set of monitoring, diagnostic, and/or therapeutic functions to the patient. The CRM device 810, the xPAP device 820, or both may include sensors for sensing conditions associated with events affecting respiration such as those identified in Tables 1-3.

In one embodiment, sensors coupled to the CRM device 810 may sense a first set of conditions associated with events affecting respiration. The sensed information may be transmitted to respiratory logbook circuitry incorporated in the xPAP device 820. Sensors coupled to the xPAP device 820 may sense a second set of conditions associated with events affecting respiration. The information sensed by the xPAP device and the CRM device may be organized by circuitry in the xPAP device into respiratory logbook format.

In another embodiment, sensors coupled to the xPAP device 820 may sense a first set of information associated with events affecting respiration and transmit the information to the CRM device. Circuitry in the CRM device may combine the information acquired by the xPAP device sensors with information acquired by sensors coupled to the CRM device to generate the respiratory logbook.

Figure 9A:
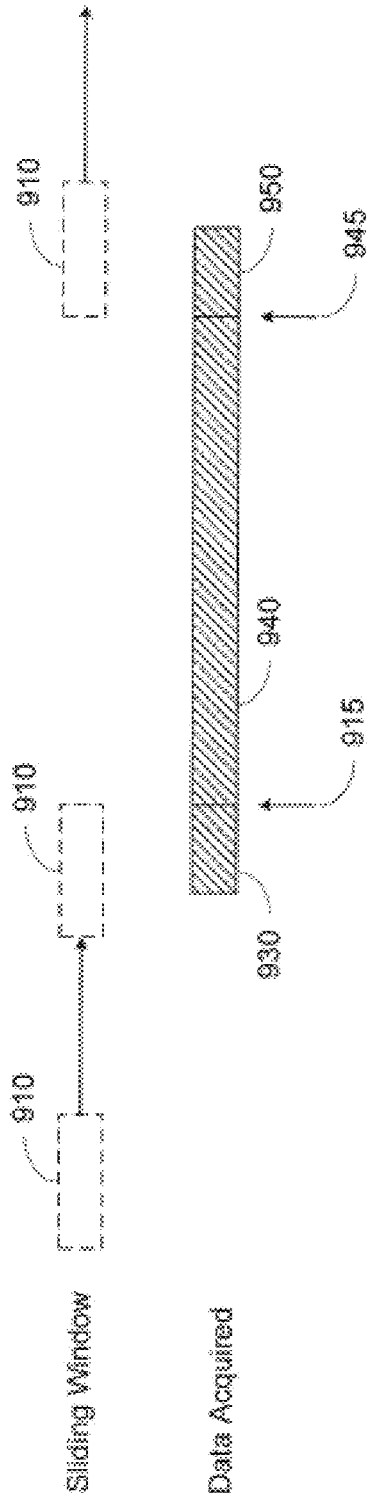
FIG. 9A provides a timing diagram illustrating the acquisition of respiration logbook information for a detected event affecting respiration in accordance with embodiments of the invention.

FIG. 9A provides a timing diagram illustrating the acquisition of respiratory logbook information for a detected event affecting respiration in accordance with embodiments of the invention. The respiratory logbook system senses and stores in a temporary buffer a sliding scale window 910 of one or more patient conditions, such as those listed in Tables 1-3. The selection of information that is sensed and stored may be programmable by the physician. The selection of the information to be acquired may be based on the patient's medical history. For example, if the patient suffers from sleep apnea, or another form of disordered breathing, the respiratory logbook would preferably be programmed to sense conditions associated with disordered breathing. Conversely, if the patient suffers from chronic obstructive pulmonary disorder, a different set of conditions from those used for disordered breathing could be sensed.

If an event affecting respiration is detected 915, then pre-event information 930 acquired prior to the event is stored. Information is collected and stored during 940 the event. Upon detection that the event has terminated 945, post-event information 950 is collected and stored for a period of time after the termination of the event. The event and post-event information 940, 950 may be acquired on a continuous basis, or the information may be acquired during discrete intervals. After the post-event information 950 is collected, the acquired information 930, 940, 950 is organized as a logbook entry. The respiratory logbook system begins sensing for the next event.

Figure 9B:
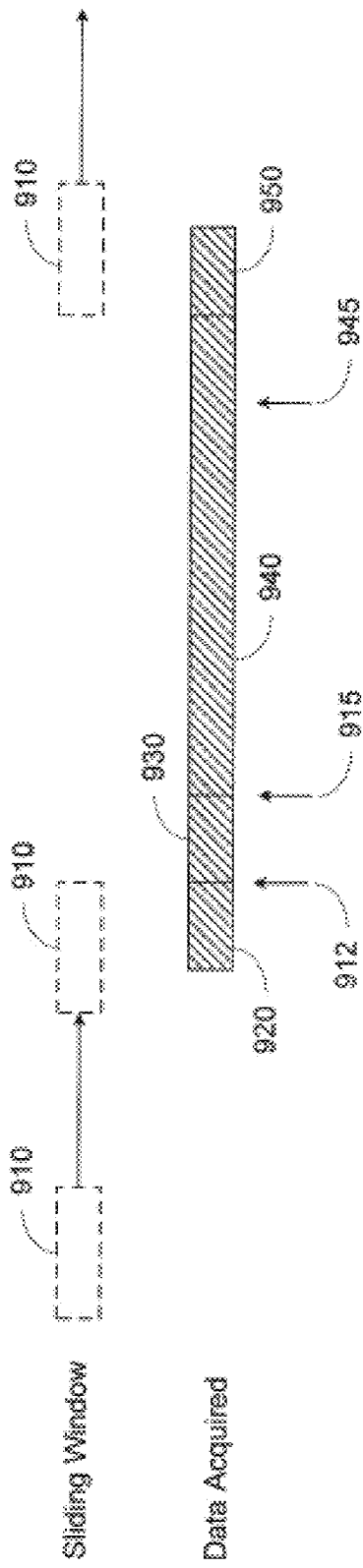
FIG. 9B provides a timing diagram illustrating the acquisition of respiratory logbook information for a predicted event affecting respiration in accordance with embodiments of the invention.

FIG. 9B provides a timing diagram illustrating the acquisition of respiratory logbook information for a predicted event affecting respiration in accordance with embodiments of the invention. The respiratory logbook system senses and stores in a temporary buffer a sliding scale window 910 of one or more patient conditions, such as those listed in Tables 1-3. The conditions that are sensed and stored are programmable and may be selected based on the patient's medical history. For example, the information sensed and stored may include information that has been effectively used to predict the one or more types of events affecting the patient's respiration. If an event affecting respiration is predicted 912, then pre-prediction information 920 is acquired and stored. When the event affecting respiration is detected 915, then pre-event information 930 acquired prior to the event is stored. Information 940 is collected and stored during the event. Upon detection that the event has terminated 945, information 950 is collected and stored for a period of time after the termination of the event. The pre-event, event and post-event information 930, 940, 950 may be acquired on a continuous basis, or the information may be acquired during discrete intervals. After the post-event information 940 is collected, the acquired information 920, 930, 940, 950 is organized as a logbook entry. The respiratory logbook begins sensing for the next event.

Figure 10A:
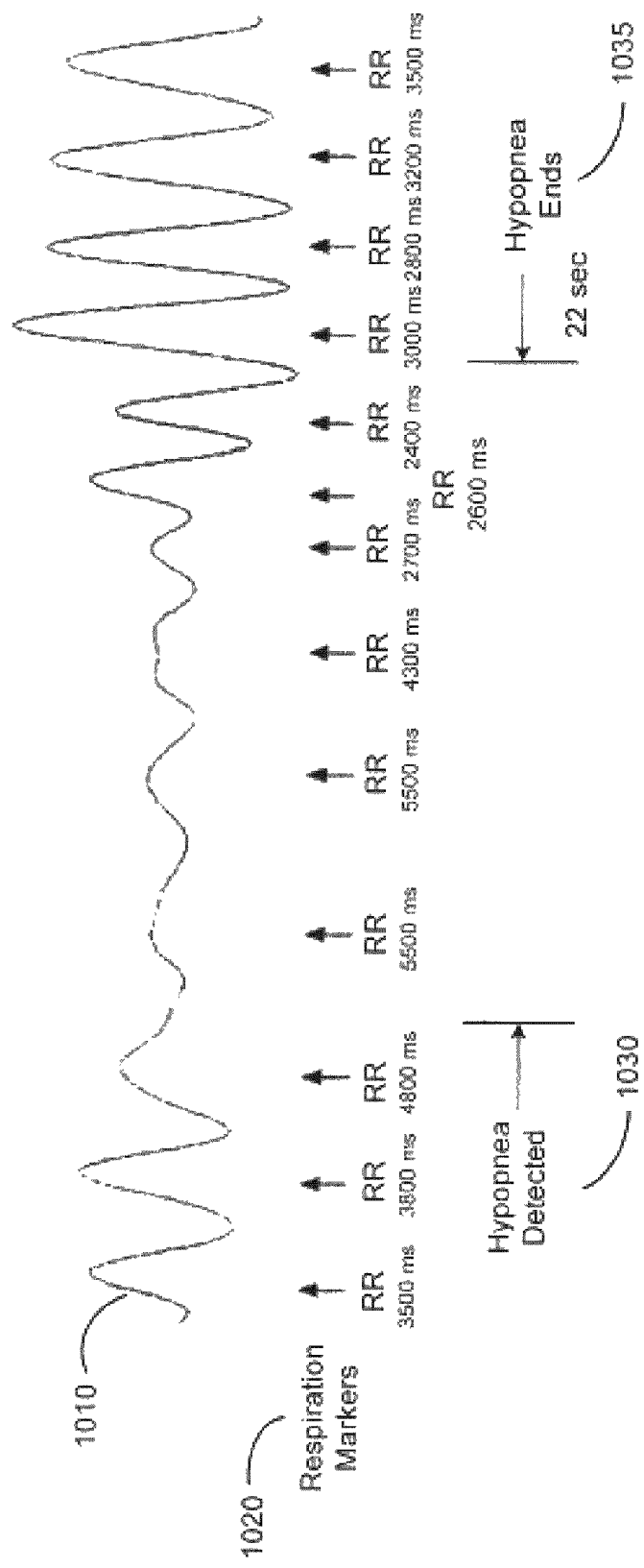
FIG. 10A illustrates a marked respiratory waveform in accordance with embodiments of the invention.
Figure 10B:
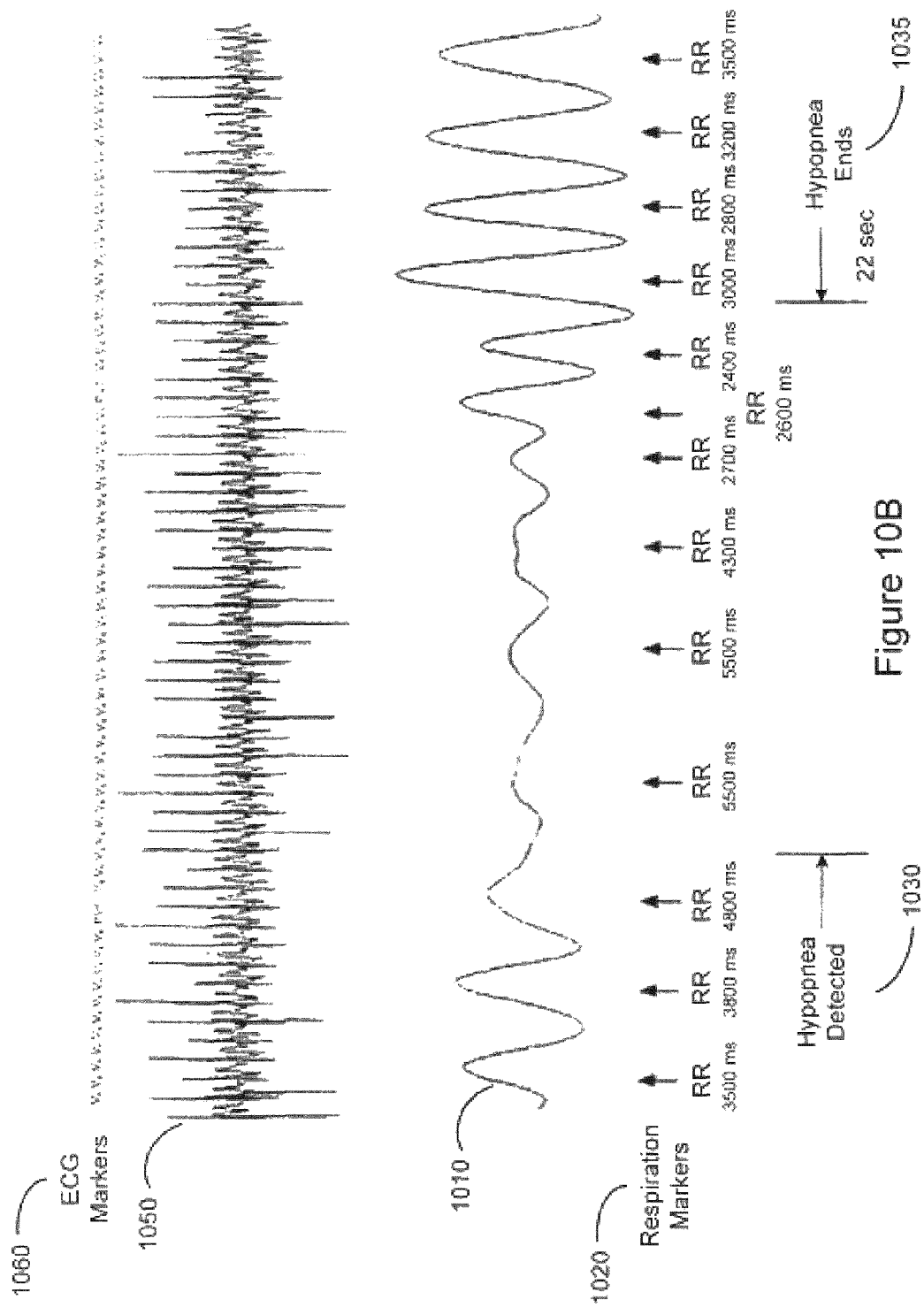
FIG. 10B illustrates a marked respiration waveform that is time aligned with an electrocardiogram (ECG) graph in accordance with embodiments of the invention.

As previously discussed in connection with FIG. 3, the respiratory logbook display may include information presented in graphical format. In one embodiment, the user may choose to view a marked respiration waveform, for example. FIGS. 10A and 10B provide examples of marked respiration waveforms that may be acquired and organized in a respiratory logbook. FIG. 10A illustrates a marked respiration waveform in accordance with embodiments of the invention. In one embodiment, information related to a marked respiration waveform may be acquired continuously as a moving snapshot of respiration-related conditions. In another embodiment, the information related to the marked respiration waveform may be acquired in response to one or more triggering events. For one example, the triggering event may comprise an instruction from a physician or through an advanced patient management system to begin data collection. In another example, the triggering event may comprise detection of various respiration conditions, such as detection of the disordered breathing, or the detection of sleep. In this scenario, the triggering event may initiate the collection of respiration-related data during an interval of time that may include time periods prior to, during, and/or following the disordered breathing event.

As illustrated in FIG. 10A, the marked respiration waveform 1010 may comprise respiration symbols positioned at locations relative to the respiration waveform to indicate when respiratory events occur or the time when characteristics are calculated. In this example, the respiration waveform 1010 is marked with respiration symbols 1020 denoting the time between peaks on the waveform and hypopnea symbols denoting when an hypopnea is detected 1030 and when an hypopnea ends 1035 after 22 seconds. In addition, other symbols indicating respiration characteristics and/or disordered breathing characteristics described above may be superimposed on the respiration waveform. The marked respiration waveform may be displayed on a display device to allow the patient's physician to view respiratory disturbances and/or other characteristics.

In addition to displaying the respiration waveform 1010, the display may show other measurements and/or other waveforms. In FIG. 10B, an electrocardiogram (ECG) 1050 is shown above respiration waveform 1010. The ECG 1050 is time-aligned with respiration waveform 1010 and can be marked with indicators corresponding to the occurrence of breathing and/or cardiac events, for example. Markers 1060 indicating sensed ventricular events (Vs) and paced ventricular events (Vp) are displayed above the ECG in FIG. 10B. Displaying marked respiration waveforms and other waveforms related to patient conditions allows the patient's physician to verify, for example, that a disordered breathing event was properly detected. This confirmation may be used to guide diagnostics and/or therapy. Symbols annotating cardiac and respiratory events provide further diagnostic information for physicians.

A number of the examples presented herein involve block diagrams illustrating functional blocks used for in accordance with embodiments of the present invention. It will be understood by those skilled in the art that there exist many possible configurations in which these functional blocks can be arranged and implemented.

The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A respiratory event logbook system, comprising:
    an event detector configured to detect or predict a respiratory event affecting the patient;
    a data acquisition unit, coupled to the event detector, and configured to collect medical information associated with the respiratory event responsive to the detection or prediction of the respiratory event;
    a processor, coupled to the data acquisition unit, and configured to organize the collected medical information associated with the respiratory event as a respiratory event log entry, wherein at least one of the event detector, the data acquisition unit, and the processor includes an implantable component; and
    a user interface coupled to the processor and configured to display at least part of the organized medical information including a time associated with the respiratory event corresponding to the displayed medical information.

2. The system of claim 1, wherein the respiratory event comprises a disordered breathing event.

3. The system of claim 1, wherein the respiratory event comprises a non-rhythm pulmonary event.

4. The system of claim 1, wherein the medical information comprises respiratory information.

5. The system of claim 1, wherein the medical information comprises cardiac information.

6. The system of claim 1, wherein:
    the data acquisition unit comprises a temporary buffer configured to temporarily store a portion of the medical information associated with the respiratory event; and
    the system further comprises a memory configured for long term storage of the medical information associated with the respiratory event.

7. The system of claim 1, wherein the medical information comprises respiratory information and cardiac information.

8. A respiratory event logbook system, comprising:
    an event detector configured to detect or predict a respiratory event affecting the patient;
    a data acquisition unit, coupled to the event detector, and configured to collect medical information associated with the respiratory event responsive to the detection or prediction of the respiratory event;
    a processor, coupled to the data acquisition unit, and configured to organize the collected medical information associated with the respiratory event as a respiratory event log entry, wherein at least one of the event detector, the data acquisition unit, and the processor includes an implantable component,
    wherein the processor is configured to organize medical information associated with a plurality of respiratory events as a respiratory event logbook; and
    a user interface, comprising a display, coupled to the processor and configured to provide access to the respiratory event logbook and to display medical information associated with the plurality of respiratory events including a time associated with each of the plurality of respiratory events corresponding to the displayed medical information.

9. The system of claim 8, wherein the user interface comprises an input mechanism configured to select one or more of the plurality of respiratory events.

10. The system of claim 8, wherein the user interface is configured to display a menu of one or more of the plurality of respiratory events.

11. The system of claim 8, wherein:
the processor is configured to generate summary information associated with one or more of the plurality of respiratory events; and
the user interface is configured to display the summary information.

12. The system of claim 8, wherein the user interface is configured to display graphical information.

13. The system of claim 8, wherein the user interface is configured to display textual information.

14. The system of claim 8, wherein the respiratory event comprises a disordered breathing event.

15. The system of claim 8, wherein the respiratory event comprises a non-rhythm pulmonary event.

16. The system of claim 8, wherein the medical information comprises respiratory information.

17. The system of claim 8, wherein the medical information comprises cardiac information.

18. The system of claim 8, wherein the medical information comprises respiratory information and cardiac information.

* * * * *